United States Patent [19]
Stiles et al.

[11] Patent Number: 5,874,269
[45] Date of Patent: Feb. 23, 1999

[54] PURIFIED PROTEINS, RECOMBINANT DNA SEQUENCES AND PROCESSES FOR CONTROLLING THE RIPENING OF COFFEE PLANT

[75] Inventors: John I. Stiles, Kaneohe; Istefo Moisyadi; Kabi Raj Neupane, both of Honolulu, all of Hi.

[73] Assignee: University of Hawaii, Honolulu, Hi.

[21] Appl. No.: 695,412

[22] Filed: Aug. 12, 1996

Related U.S. Application Data

[63] Continuation-in-part of Ser. No. 485,107, Jun. 7, 1995, Pat. No. 5,767,376.
[51] Int. Cl.$^6$ .............................. C12N 9/02; C12N 9/88; C12N 15/29; C12N 15/00; A01H 5/00; A01H 5/10
[52] U.S. Cl. .................. 435/189; 536/23.6; 435/232; 435/183; 435/468; 435/320.1; 800/278; 800/283; 800/285; 800/286; 800/298
[58] Field of Search ........................ 536/23.6; 435/172.3, 435/189, 183, 232, 468, 320.1; 47/58; 800/278, 283, 285, 286, 298

[56] References Cited

U.S. PATENT DOCUMENTS

| | | |
|---|---|---|
| 5,304,490 | 4/1994 | Bird et al. . |
| 5,334,529 | 8/1994 | Adams et al. . |
| 5,356,799 | 10/1994 | Fabijanski et al. . |
| 5,364,780 | 11/1994 | Hershey et al. . |
| 5,365,015 | 11/1994 | Grierson et al. . |
| 5,367,065 | 11/1994 | Ecker et al. . |
| 5,416,250 | 5/1995 | Ferro et al. . |
| 5,436,395 | 7/1995 | Sondahl et al. . |
| 5,444,166 | 8/1995 | Ecker et al. . |
| 5,449,764 | 9/1995 | Bird et al. . |
| 5,451,514 | 9/1995 | Boudet et al. . |
| 5,453,566 | 9/1995 | Shewmaker et al. . |
| 5,457,041 | 10/1995 | Ginavan et al. . |
| 5,530,190 | 6/1996 | Grierson et al. . |

FOREIGN PATENT DOCUMENTS

| | | |
|---|---|---|
| WO 91/01375 | 2/1991 | WIPO . |
| WO 92/04456 | 3/1992 | WIPO . |
| WO 9533377 | of 1995 | WIPO . |
| WO 96/07742 | 3/1996 | WIPO . |
| WO 96/19103 | 6/1996 | WIPO . |
| WO 96/21027 | 7/1996 | WIPO . |

OTHER PUBLICATIONS

"Are Xanthosine and 7–Methylxanthosine Caffeine Precursors?" by Schulthess Baumann Phyto chemistry 39(6):1363–1370, 1995.

"A Visible Marker for Antisense mRNA expression in plants: Inhibition of chlorophyll synthesis with a glutamate–1–semialdehyde aminotransferase antisense gene" by Höfgen, et al. (Proc. Natl. Acad. Sci. USA, vol. 91, pp. 1726–1730, Mar. 1994, Plant Biology).

"Purine and Purine Alkalois Metabolism in Camellia and Coffea Plants" by Suzuki, et al. (Phytochemistry Review Article No. 68, 1992, vol. 31, No. 8, pp. 2575–2584).

"Modifying Fruit Ripening by Suppressing Gene Expression" by Athanasois Theologis, Paul W. Oeller and Lu Min–Wong; 1993, pp. 19–23, Cellular & Molecular Aspects of the Plant Hormone Ethylene, ed. Pech et al, Klyver Academic Pub.

"One Rotten Apple Spoils the Whole Bushel: The Role of Ethylene in Fruit Ripening" by Athanasois Theologis Cell 70:181–184 (1992).

"Reversible Inhibition of Tomato Fruit Senescence by Antisence RNA" by Paul W. Oeller, Lu Min–Wong, Loverine P. Taylor, Deborah A. Pike, Athanasois Theologis, Science, Oct. 1991 pp. 437–439.

Schuch, U.K. et al. Journal of the American Society for Horticultural Science, vol. 177, pp. 158–163 (abstract only), 1992.

Theologis, A. et al. Developmental Genetics, vol. 14, pp. 285–295 (abstract only), 1993.

Nagata, M. et al. Acta Horticulture, No. 394, pp. 213–218 (abstract only), 1995.

Smith, C.J.S. et al. Nature, vol. 334, p. 724–726.

*Primary Examiner*—Mary E. Mosher
*Attorney, Agent, or Firm*—Jones, Day, Reavis & Pogue

[57] ABSTRACT

The invention provides purified proteins, DNA sequences that code on expression therefore and recombinant DNA molecules, including hosts transformed therewith for transforming coffee plants to suppress the expression of enzymes necessary for ethylene synthesis. The DNA sequences and recombinant DNA molecules are characerized in that they code on expression for the enzymes ACC synthase or ACC oxidase that are elements of the pathway for ethylene biosynthesis in coffee plants. Coffee plants are transformed with vectors containing ACC synthase and/or with ACC oxidase DNA sequences that code on expression for the respective mRNA that is antisense to the mRNA for ACC synthase and/or ACC oxidase. The resulting antisense mRNA binds to the respective ACC synthase and/or ACC oxidase mRNA, thereby inactivating the mRNA encoding one or more enzymes in the pathway for ethylene synthesis. The described DNA sequences can also be used to block synthesis of ACC synthase or ACC oxidase using co-suppression. The result in either event is that the transformed plants are incapable of synthesizing ethylne, though other aspects of their metabolism is not affected.

48 Claims, 11 Drawing Sheets

**FIGURE 1: DEDUCED AMINO ACID SEQUENCE OF ACC SYNTHASE FROM *COFFEA ARABICA* (SEQ ID NO:10)**

```
Met Glu Phe Ser Leu Lys Asn Glu Gln Gln Gln Leu Leu Ser Lys
 1            5                  10                      15
Met Ala Thr Asn Asp Gly His Gly Glu Asn Ser Pro Tyr Phe Asp
              20                  25                      30
Gly Trp Lys Ala Tyr Asp Ser Asp Pro Tyr His Pro Thr Arg Asn
              35                  40                      45
Pro Asn Gly Val Ile Gln Met Gly Leu Ala Glu Asn Gln Leu Cys
              50                  55                      60
Phe Asp Leu Ile Glu Glu Trp Val Leu Asn Asn Pro Glu Ala Ser
              65                  70                      75
Ile Cys Thr Ala Glu Gly Ala Asn Lys Phe Met Glu Val Ala Ile
              80                  85                      90
Tyr Gln Asp Tyr His Gly Leu Pro Glu Phe Arg Asn Ala Val Ala
              95                 100                     105
Arg Phe Met Glu Lys Val Arg Gly Asp Arg Val Lys Phe Asp Pro
             110                 115                     120
Asn Arg Ile Val Met Ser Gly Gly Ala Thr Gly Ala His Glu Thr
             125                 130                     135
Leu Ala Phe Cys Leu Ala Asp Pro Glu Asp Ala Phe Leu Val Pro
             140                 145                     150
Thr Pro Tyr Tyr Pro Gly Phe Asp Arg Asp Leu Arg Trp Arg Thr
             155                 160                     165
Gly Met Gln Leu Leu Pro Ile Val Cys Arg Ser Ser Asn Asp Phe
             170                 175                     180
Lys Val Thr Lys Glu Ser Met Glu Ala Ala Tyr Gln Lys Ala Gln
             185                 190                     195
Glu Ala Asn Ile Arg Val Lys Gly Phe Leu Leu Asn Asn Pro Ser
             200                 205                     210
Asn Pro Leu Gly Thr Val Leu Asp Arg Glu Thr Leu Ile Asp Ile
             215                 220                     225
Val Thr Phe Ile Asn Asp Lys Asn Ile His Leu Ile Cys Asp Glu
             230                 235                     240
```

FIGURE 1 (continued)

```
Ile Tyr Ser Ala Thr Val Phe Ser Gln Pro Glu Phe Ile Ser Ile
            245             250             255
Ser Glu Ile Ile Glu His Asp Val Gln Cys Asn Arg Asp Leu Ile
            260             265             270
His Leu Val Tyr Ser Leu Ser Lys Asp Leu Gly Phe Pro Gly Phe
            275             280             285
Arg Val Gly Ile Leu Tyr Ser Tyr Asn Asp Ala Val Val Ser Cys
            290             295             300
Ala Arg Lys Met Ser Ser Phe Gly Leu Val Ser Thr Gln Thr Gln
            305             310             315
His Leu Ile Ala Ser Met Leu Ser Asp Glu Ala Phe Met Asp Lys
            320             325             330
Ile Ile Ser Thr Ser Ser Glu Arg Leu Ala Ala Arg His Gly Leu
            335             340             345
Phe Thr Arg Gly Leu Ala Gln Val Gly Ile Gly Thr Leu Lys Ser
            350             355             360
Ser Ala Gly Leu Tyr Phe Trp Met Asp Leu Arg Arg Leu Leu Arg
            365             370             375
Glu Ser Thr Phe Glu Ala Glu Met Glu Leu Trp Arg Ile Ile Ile
            380             385             390
His Glu Val Lys Leu Asn Val Ser Pro Gly Leu Ser Phe His Cys
            395             400             405
Ser Glu Pro Gly Trp Phe Arg Val Cys Phe Ala Asn Met Asp Asp
            410             415             420
Glu Ser Val Arg Val Ala Leu Arg Arg Ile His Lys Phe Val Leu
            425             430             435
Val Gln Gly Lys Ala Thr Glu Pro Thr Thr Pro Lys Ser Arg Cys
            440             445             450
Gly Ser Ser Lys Leu Gln Leu Ser Leu Ser Phe Arg Arg Leu Asp
            455             460             465
Glu Arg Val Met Gly Ser His Met Met Ser Pro His Ser Pro Met
            470             475             480
Ala Ser Pro Leu Val Arg Ala Thr
            485
```

FIGURE 2: COFFEE FRUIT-EXPRESSED ACC SYNTHASE GENE SEQUENCE
(SEQ ID NO:11)

```
GTAATCTCTT CTAAAATCAA CCATTCTCTT CATTCTTCAC TTGACAAGGC         50

CACTGCATTC TTCATTCTTT CTTGATATAT AGCCATTTTT TTCATTCTTT        100

CTTGATATAT AGCCATTTTT TTCATTCTTT CTTCATTCAT TGTCTGGAGA        150

AGTTGGTTGA GTTTTCTTGA AAATTCAAGC AAAACA ATG GAG TTC AGT       198
                                         Met Glu Phe Ser
                                          1

TTG AAA AAC GAA CAA CAA CAA CTC TTG TCG AAG ATG GCA ACC       240
Leu Lys Asn Glu Gln Gln Gln Leu Leu Ser Lys Met Ala Thr
 5              10                  15

AAC GAT GGA CAT GGC GAA AAC TCG CCT TAT TTT GAT GGT TGG       282
Asn Asp Gly His Gly Glu Asn Ser Pro Tyr Phe Asp Gly Trp
     20              25                  30

AAG GCA TAT GAT AGT GAT CCT TAC CAT CCC ACC AGA AAT CCT       324
Lys Ala Tyr Asp Ser Asp Pro Tyr His Pro Thr Arg Asn Pro
         35              40                  45

AAT GGT GTT ATA CAG ATG GGA CTC GCA GAA AAT CAG TTA TGC       366
Asn Gly Val Ile Gln Met Gly Leu Ala Glu Asn Gln Leu Cys
             50                  55                  60

TTT GAT TTG ATC GAG GAA TGG GTT CTG AAC AAT CCA GAG GCT       408
Phe Asp Leu Ile Glu Glu Trp Val Leu Asn Asn Pro Glu Ala
                 65                  70

TCC ATT TGC ACA GCA GAA GGA GCG AAC AAA TTC ATG GAA GTT       450
Ser Ile Cys Thr Ala Glu Gly Ala Asn Lys Phe Met Glu Val
 75                  80                  85

GCT ATC TAT CAA GAT TAT CAT GGC TTG CCA GAG TTC AGA AAT       492
Ala Ile Tyr Gln Asp Tyr His Gly Leu Pro Glu Phe Arg Asn
         90                  95                 100

GCT GTA GCA AGG TTC ATG GAG AAG GTG AGA GGT GAC AGA GTC       534
Ala Val Ala Arg Phe Met Glu Lys Val Arg Gly Asp Arg Val
            105                 110                 115
```

FIGURE 2 (continued)

| | | | | | | | | | | | | | |
|---|---|---|---|---|---|---|---|---|---|---|---|---|---|
| AAG | TTC | GAT | CCC | AAC | CGC | ATT | GTG | ATG | AGT | GGT | GGG | GCA | ACC | 576 |
| Lys | Phe | Asp | Pro | Asn | Arg | Ile | Val | Met | Ser | Gly | Gly | Ala | Thr | |
| | | | 120 | | | | | 125 | | | | | 130 | |

| | | | | | | | | | | | | | |
|---|---|---|---|---|---|---|---|---|---|---|---|---|---|
| GGA | GCT | CAT | GAA | ACT | CTG | GCC | TTC | TGT | TTA | GCT | GAC | CCT | GAA | 618 |
| Gly | Ala | His | Glu | Thr | Leu | Ala | Phe | Cys | Leu | Ala | Asp | Pro | Glu | |
| | | | | 135 | | | | | 140 | | | | | |

| | | | | | | | | | | | | | |
|---|---|---|---|---|---|---|---|---|---|---|---|---|---|
| GAT | GCG | TTT | TTG | GTA | CCC | ACA | CCA | TAT | TAT | CCA | GGA | TTT | GAT | 660 |
| Asp | Ala | Phe | Leu | Val | Pro | Thr | Pro | Tyr | Tyr | Pro | Gly | Phe | Asp | |
| 145 | | | | | 150 | | | | | 155 | | | | |

| | | | | | | | | | | | | | |
|---|---|---|---|---|---|---|---|---|---|---|---|---|---|
| CGG | GAT | TTG | AGG | TGG | CGA | ACA | GGG | ATG | CAA | CTT | CTT | CCA | ATT | 702 |
| Arg | Asp | Leu | Arg | Trp | Arg | Thr | Gly | Met | Gln | Leu | Leu | Pro | Ile | |
| | | 160 | | | | | 165 | | | | | 170 | | |

| | | | | | | | | | | | | | |
|---|---|---|---|---|---|---|---|---|---|---|---|---|---|
| GTT | TGT | CGC | AGC | TCC | AAT | GAT | TTT | AAG | GTC | ACT | AAA | GAA | TCC | 744 |
| Val | Cys | Arg | Ser | Ser | Asn | Asp | Phe | Lys | Val | Thr | Lys | Glu | Ser | |
| | | | 175 | | | | | 180 | | | | | 185 | |

| | | | | | | | | | | | | | |
|---|---|---|---|---|---|---|---|---|---|---|---|---|---|
| ATG | GAA | GCT | GCT | TAT | CAG | AAA | GCT | CAA | GAA | GCC | AAC | ATC | AGA | 786 |
| Met | Glu | Ala | Ala | Tyr | Gln | Lys | Ala | Gln | Glu | Ala | Asn | Ile | Arg | |
| | | | | 190 | | | | | 195 | | | | | 200 |

| | | | | | | | | | | | | | |
|---|---|---|---|---|---|---|---|---|---|---|---|---|---|
| GTA | AAG | GGG | TTC | CTC | TTA | AAT | AAT | CCA | TCA | AAT | CCA | TTG | GGA | 828 |
| Val | Lys | Gly | Phe | Leu | Leu | Asn | Asn | Pro | Ser | Asn | Pro | Leu | Gly | |
| | | | | 205 | | | | | 210 | | | | | |

| | | | | | | | | | | | | | |
|---|---|---|---|---|---|---|---|---|---|---|---|---|---|
| ACT | GTT | CTT | GAC | AGG | GAA | ACT | TTG | ATT | GAT | ATA | GTC | ACA | TTC | 870 |
| Thr | Val | Leu | Asp | Arg | Glu | Thr | Leu | Ile | Asp | Ile | Val | Thr | Phe | |
| 215 | | | | | 220 | | | | | 225 | | | | |

| | | | | | | | | | | | | | |
|---|---|---|---|---|---|---|---|---|---|---|---|---|---|
| ATC | AAT | GAC | AAA | AAT | ATC | CAC | TTG | ATT | TGT | GAT | GAG | ATA | TAT | 912 |
| Ile | Asn | Asp | Lys | Asn | Ile | His | Leu | Ile | Cys | Asp | Glu | Ile | Tyr | |
| | | 230 | | | | | 235 | | | | | 240 | | |

| | | | | | | | | | | | | | |
|---|---|---|---|---|---|---|---|---|---|---|---|---|---|
| TCT | GCC | ACC | GTC | TTC | AGC | CAG | CCC | GAA | TTC | ATC | AGC | ATC | TCT | 954 |
| Ser | Ala | Thr | Val | Phe | Ser | Gln | Pro | Glu | Phe | Ile | Ser | Ile | Ser | |
| | | | 245 | | | | | 250 | | | | | 255 | |

FIGURE 2 (continued)

```
GAA ATA ATT GAG CAT GAT GTT CAA TGC AAC CGT GAT CTC ATA        996
Glu Ile Ile Glu His Asp Val Gln Cys Asn Arg Asp Leu Ile
            260             265                 270

CAT CTT GTG TAT AGC CTG TCC AAG GAC TTG GGC TTC CCT GGA       1038
His Leu Val Tyr Ser Leu Ser Lys Asp Leu Gly Phe Pro Gly
                275             280

TTC AGA GTT GGC ATT TTG TAT TCA TAT AAT GAC GCT GTT GTC       1080
Phe Arg Val Gly Ile Leu Tyr Ser Tyr Asn Asp Ala Val Val
285             290             295

AGC TGT GCT AGA AAA ATG TCG AGT TTC GGC CTT GTT TCA ACA       1122
Ser Cys Ala Arg Lys Met Ser Ser Phe Gly Leu Val Ser Thr
        300             305             310

CAA ACT CAG CAT CTG ATT GCA TCA ATG TTA TCG GAC GAA GCA       1164
Gln Thr Gln His Leu Ile Ala Ser Met Leu Ser Asp Glu Ala
            315             320             325

TTT ATG GAC AAA ATC ATT TCC ACG AGC TCA GAG AGA TTA GCT       1206
Phe Met Asp Lys Ile Ile Ser Thr Ser Ser Glu Arg Leu Ala
                330             335             340

GCA AGG CAT GGT CTT TTC ACA AGA GGA CTT GCT CAA GTA GGC       1248
Ala Arg His Gly Leu Phe Thr Arg Gly Leu Ala Gln Val Gly
                    345             350

ATT GGC ACC TTA AAA AGC AGT GCG GGC CTT TAT TTC TGG ATG       1290
Ile Gly Thr Leu Lys Ser Ser Ala Gly Leu Tyr Phe Trp Met
355             360             365

GAC TTA AGG AGA CTC CTC AGG GAG TCC ACA TTT GAG GCA GAA       1332
Asp Leu Arg Arg Leu Leu Arg Glu Ser Thr Phe Glu Ala Glu
        370             375             380

ATG GAA CTT TGG AGG ATC ATA ATA CAT GAA GTC AAG CTC AAT       1374
Met Glu Leu Trp Arg Ile Ile Ile His Glu Val Lys Leu Asn
            385             390             395
```

FIGURE 2 (continued)

```
GTT TCA CCA GGC TTA TCT TTC CAT TGC TCA GAA CCA GGA TGG       1416
Val Ser Pro Gly Leu Ser Phe His Cys Ser Glu Pro Gly Trp
        400                 405                 410

TTC AGA GTT TGC TTT GCC AAC ATG GAC GAC GAA AGT GTG AGA       1458
Phe Arg Val Cys Phe Ala Asn Met Asp Asp Glu Ser Val Arg
                415                 420

GTT GCT CTC AGA AGA ATC CAC AAA TTT GTG CTT GTT CAG GGC       1500
Val Ala Leu Arg Arg Ile His Lys Phe Val Leu Val Gln Gly
425                 430                 435

AAG GCA ACA GAG CCA ACA ACT CCA AAG AGT CGC TGC GGA AGC       1542
Lys Ala Thr Glu Pro Thr Thr Pro Lys Ser Arg Cys Gly Ser
        440                 445                 450

AGC AAA CTT CAA CTC AGC TTA TCT TTC CGC AGA TTG GAC GAA       1584
Ser Lys Leu Gln Leu Ser Leu Ser Phe Arg Arg Leu Asp Glu
        455                 460                 465

AGG GTG ATG GGA TCG CAT ATG ATG TCC CCT CAC TCC CCG ATG       1626
Arg Val Met Gly Ser His Met Met Ser Pro His Ser Pro Met
                470                 475                 480

GCT TCA CCT TTG GTT CGG GCT ACA TAAATCATTT CTTGATCAGA         1670
Ala Ser Pro Leu Val Arg Ala Thr
                485

TCATATAGCA AAGATTCCTG AGTAAATACT CGAAACCCTT TCTGGATAAC        1720

TGAAAAGAGA GTTGTTGATT CTTTGCTGTA TCATACAAAC ACGTTACAGG        1770

CATTTTTTGG CCATCTGATG CGTGCAAATT GCATCAAATG CTTTTATTAT        1820

TGTCATATTC ATTTGTGTAC CTTGGTTTTC CTTGCCCTTC AGTCCTCCTT        1870

GTTTTTTGTT TCTTTGTTAT TATTTTCTTC CAGTTGATCA GTTAAACGAA        1920

GGAAGCTCAA TTGTTTCAAG CTATTAGTAA CAGATCATTT TGTAATAGCA        1970

ATAGTTTCAG GATTCTGAAA TGAAAGTTTA TCATTTTTCC ATCATTTTAA        2020

AAAAAAAAAA AAAAAAAAA                                         2040
```

FIGURE 3: DEDUCED PROTEIN SEQUENCE OF THE COFFEE FRUIT-EXPRESSED ACC OXIDASE cDNA (SEQ ID NO:12)

```
Met Ala Thr Phe Pro Leu Ile Asp Met Glu Lys Leu Asp Gly Glu
 1               5              10                  15

Glu Arg Ala Ala Thr Met Gly Val Ile Lys Asp Ala Cys Glu Ser
                 20              25                  30

Trp Gly Phe Phe Glu Val Leu Asn His Gly Ile Ser Asn Glu Leu
                 35              40                  45

Met Asp Thr Val Glu Arg Leu Thr Lys Glu His Tyr Lys Lys Cys
                 50              55                  60

Met Glu Leu Lys Phe Lys Glu Met Val Glu Ser Lys Glu Leu Glu
                 65              70                  75

Ala Val Gln Thr Glu Ile Asn Asp Leu Asp Trp Glu Ser Thr Phe
                 80              85                  90

Phe Leu Arg His Leu Pro Val Ser Asn Ile Ser Glu Val Pro Asp
                 95             100                 105

Leu Asp Asp Glu Tyr Arg Lys Val Met Lys Glu Phe Ala Leu Gln
                110             115                 120

Leu Glu Lys Leu Ala Glu Leu Leu Leu Asp Leu Leu Cys Glu Asn
                125             130                 135

Leu Gly Leu Glu Lys Gly Tyr Leu Lys Lys Ala Phe Tyr Gly Thr
                140             145                 150

Lys Gly Pro Thr Phe Gly Thr Lys Val Ser Asn Tyr Pro Pro Cys
                155             160                 165

Pro Arg Pro Glu Leu Ile Lys Gly Leu Arg Ala His Thr Asp Ala
                170             175                 180

Gly Gly Ile Ile Leu Leu Phe Gln Asp Asp Lys Val Ser Gly Leu
                185             190                 195

Gln Leu Leu Lys Asp Gly Glu Trp Val Asp Val Pro Pro Met Arg
                200             205                 210

His Ser Ile Val Ile Asn Ile Gly Asp Gln Leu Glu Val Ile Thr
                215             220                 225

Asn Gly Lys Tyr Lys Ser Val Met His Arg Val Ile Ala Gln Pro
                230             235                 240
```

FIGURE 3 (continued)

```
Asp Gly Asn Arg Met Ser Leu Ala Ser Phe Tyr Asn Pro Gly Ser
                245                 250                 255

Asp Ala Val Ile Tyr Pro Ala Pro Ala Leu Val Glu Lys Glu Ala
                260                 265                 270

Glu Asp Lys Gln Ile Tyr Pro Lys Phe Val Phe Glu Asp Tyr Met
                275                 280                 285

Lys Leu Tyr Ala Gly Leu Lys Phe Gln Ala Lys Glu Pro Arg Phe
                290                 295                 300

Glu Ala Met Lys Ala Val Glu Ser Thr Val Asn Leu Gly Pro Ile
                305                 310                 315

Ala Thr Val
        318
```

FIGURE 4: DNA SEQUENCE OF THE COFFEE FRUIT-EXPRESSED ACC OXIDASE
cDNA (SEQ ID NO:13)

```
TGTAAACGAA GCATAAGCAC AAGCAAACAC AAACTAGAAA GAGAG ATG              48
                                                   Met
                                                    1

GCT ACA TTC CCC CTA ATC GAC ATG GAG AAG CTT GAC GGT GAA             90
Ala Thr Phe Pro Leu Ile Asp Met Glu Lys Leu Asp Gly Glu
            5               10                      15

GAG AGG GCT GCC ACT ATG GGA GTC ATA AAA GAT GCT TGT GAA            132
Glu Arg Ala Ala Thr Met Gly Val Ile Lys Asp Ala Cys Glu
                20                  25

AGC TGG GGC TTC TTT GAG GTG TTG AAT CAT GGG ATA TCT AAT            174
Ser Trp Gly Phe Phe Glu Val Leu Asn His Gly Ile Ser Asn
30                      35                  40

GAG CTC ATG GAC ACA GTG GAG AGG CTA ACA AAG GAG CAT TAC            216
Glu Leu Met Asp Thr Val Glu Arg Leu Thr Lys Glu His Tyr
        45                  50                  55

AAG AAA TGT ATG GAA CTA AAG TTC AAG GAA ATG GTG GAG AGC            258
Lys Lys Cys Met Glu Leu Lys Phe Lys Glu Met Val Glu Ser
            60                  65                  70

AAG GAA TTG GAA GCT GTT CAG ACT GAG ATC AAT GAT TTG GAC            300
Lys Glu Leu Glu Ala Val Gln Thr Glu Ile Asn Asp Leu Asp
                75                  80                  85

TGG GAA AGT ACC TTC TTC TTG CGC CAT CTT CCT GTT TCC AAC            342
Trp Glu Ser Thr Phe Phe Leu Arg His Leu Pro Val Ser Asn
                    90                  95

ATC TCA GAA GTC CCT GAT CTT GAT GAT GAA TAC AGA AAG GTT            384
Ile Ser Glu Val Pro Asp Leu Asp Asp Glu Tyr Arg Lys Val
100                 105                 110

ATG AAG GAA TTT GCG TTG CAA CTT GAG AAA CTA GCA GAG CTC            426
Met Lys Glu Phe Ala Leu Gln Leu Glu Lys Leu Ala Glu Leu
        115                 120                 125
```

FIGURE 4 (continued)

```
CTG TTG GAC TTG CTA TGC GAG AAC CTT GGC CTA GAG AAA GGC         468
Leu Leu Asp Leu Leu Cys Glu Asn Leu Gly Leu Glu Lys Gly
        130                 135                 140

TAT CTG AAG AAA GCC TTC TAT GGC ACC AAA GGA CCA ACC TTT         510
Tyr Leu Lys Lys Ala Phe Tyr Gly Thr Lys Gly Pro Thr Phe
            145                 150                 155

GGC ACC AAA GTC AGC AAT TAC CCT CCA TGC CCT CGT CCA GAA         552
Gly Thr Lys Val Ser Asn Tyr Pro Pro Cys Pro Arg Pro Glu
                160                 165

CTG ATC AAG GGC CTC CGG GCA CAC ACC GAT GCC GGC GGC ATC         594
Leu Ile Lys Gly Leu Arg Ala His Thr Asp Ala Gly Gly Ile
170                 175                 180

ATC CTG CTG TTC CAG GAT GAC AAG GTC AGC GGT CTC CAG CTC         636
Ile Leu Leu Phe Gln Asp Asp Lys Val Ser Gly Leu Gln Leu
        185                 190                 195

CTC AAG GAT GGT GAA TGG GTG GAT GTT CCG CCT ATG CGC CAC         678
Leu Lys Asp Gly Glu Trp Val Asp Val Pro Pro Met Arg His
            200                 205                 210

TCC ATT GTA ATC AAC ATC GGC GAC CAA CTT GAG GTA ATC ACA         720
Ser Ile Val Ile Asn Ile Gly Asp Gln Leu Glu Val Ile Thr
                215                 220                 225

AAT GGA AAA TAC AAG AGT GTG ATG CAC CGG GTG ATA GCT CAA         762
Asn Gly Lys Tyr Lys Ser Val Met His Arg Val Ile Ala Gln
                    230                 235

CCA GAT GGG AAC AGA ATG TCA CTA GCA TCA TTC TAC AAT CCA         804
Pro Asp Gly Asn Arg Met Ser Leu Ala Ser Phe Tyr Asn Pro
240                 245                 250

GGA AGT GAT GCA GTG ATC TAT CCA GCA CCG GCA TTG GTT GAG         846
Gly Ser Asp Ala Val Ile Tyr Pro Ala Pro Ala Leu Val Glu
        255                 260                 265
```

FIGURE 4 (continued)

```
AAA GAG GCA GAG GAC AAG CAG ATA TAT CCC AAG TTT GTG TTC       888
Lys Glu Ala Glu Asp Lys Gln Ile Tyr Pro Lys Phe Val Phe
        270             275             280

GAG GAC TAC ATG AAG CTC TAT GCT GGC CTT AAG TTC CAA GCT       930
Glu Asp Tyr Met Lys Leu Tyr Ala Gly Leu Lys Phe Gln Ala
            285             290             295

AAA GAG CCC AGG TTT GAA GCC ATG AAG GCC GTG GAA AGC ACC       972
Lys Glu Pro Arg Phe Glu Ala Met Lys Ala Val Glu Ser Thr
                300             305

GTA AAC TTG GGT CCA ATC GCA ACT GTT TGAGATAATA CACGCTTTGA    1019
Val Asn Leu Gly Pro Ile Ala Thr Val
310             315

TCTGCTGCTG TCTTATAATG CGCGTTTGCG TAATCATATC CTAGCATAGT       1069

ATATCTGAGA TCTGAGTCTG TATTGTGGTG TGAGTTTGGT TTAGCCCCTT       1119

GTTAATGCTT GGATTGGACT AGTTAAATGT GGAGCTGGTT TGTTAGATAA       1169

GATAGTCTTG CCAGGATCTT TGAGTAAATA TGATTCTGCG GAAGTCTGCG       1219

GTGAATGATA ACGTGTAAAG CAATCCGAAA GTTACCTTTC TGGGGCTTTG       1269

TCATATGCAA TGGAGAAGGA ATCTTCCAAA AAAAAAAAAA AAAAAAAAA        1319

A                                                            1320
```

PURIFIED PROTEINS, RECOMBINANT DNA SEQUENCES AND PROCESSES FOR CONTROLLING THE RIPENING OF COFFEE PLANT

This application is a continuation-in-part of Ser. No. 08/485,107 filed Jun. 7, 1995, now U.S. Pat. No. 5,767,376.

FIELD OF THE INVENTION

This application relates to purified proteins, recombinant DNA sequences, hosts transformed therewith and processes for controlling the ripening of coffee plants. More particularly, this application relates to purified proteins, and recombinant DNA sequences that can be used to suppress the expression of coffee fruit-specific 1-aminocyclopropane-1-carboxylic acid (ACC) synthase and ACC oxidase genes. This application further relates to coffee plants transformed with such sequences, thereby rendered incapable of synthesizing ethylene necessary for ripening. Application of exogenous ethylene to plants transformed in accordance with this invention makes it possible to synchronize and control fruit ripening in coffee plants.

BACKGROUND OF THE INVENTION

Coffee is prepared from the roasted beans of the plants of the genus Coffea, generally from the species C. arabica. Beans are the seeds of the coffee plant and are obtained by processing the fruit, most ideally mature fruit which commands the best price due to its superior quality. In the past, high quality "gourmet" coffee was hand picked. This is necessary because the fruits of a coffee tree do not ripen uniformly and thus there are both mature and immature fruit on the same tree. In the past, this was not a serious problem as most coffee is grown in areas of the world where labor is plentiful and not expensive. However, more recently lack of abundant and inexpensive labor has become a major contributor to decreased productivity in coffee production. To increase productivity some regions of the world, such as the largest coffee producing country, Brazil, have resorted to strip harvesting where workers rapidly remove all fruit from a branch whether ripe or unripe. This increases the speed of harvesting but decreases the yield of the highest quality beans as much of the fruit is immature (green).

Furthermore, the lack of uniform ripening has seriously limited the effectiveness of mechanical harvesting. The force required to remove mature fruit (cherry) from the tree is similar to the force required to remove green fruit. Thus, mechanical harvesters do not distinguish well between green and cherry and a large amount of immature fruit is harvested along with mature fruit. This greatly decreases the yield of mature fruit and limits productivity. If coffee fruit ripening could be controlled so that all fruit ripened at one time, both the strip method of hand harvesting and mechanical harvesting would be much more efficient and a higher percentage of the harvested fruit would be in the higher quality grades. This would increase profitability of coffee production.

As is the case with many other fruit [Yang and Hoffman, Ann. Rev. Plant Physiol. 35:155 (1984)], plant-produced ethylene plays an important role in the final stages of fruit ripening in coffee. Once coffee fruit reach a certain stage of maturity they can be induced to ripen by the exogenous application of ethylene [Crisosto, C. H., P. C. Tausend, M. A. Nagao, L. H. Fuchigami and T. H. H. Chen, J. Haw. Pac. Agri. 3:13–17 (1991). This demonstrates the importance of ethylene for the final stages of fruit ripening in coffee.

Ethylene is synthesized in a two-step reaction from S-adenosylmethionine (SAM). The first step is the synthesis of 1-aminocyclopropane-1-carboxylic acid (ACC) from SAM by ACC synthase. In most plants this is the rate limiting step. The final step is the conversion of ACC to ethylene which is catalyzed by ACC oxidase (Yang and Hoffman, supra). Inhibition of ethylene biosynthesis by chemical (e.g., silver ions or carbon dioxide) or biotechnological means [Oeller et al., Science 254:437 (1991)] inhibits the final stages of ripening. This inhibition is reversible by the application of ethylene.

Accordingly, a strategy for controlling the ripening of coffee plants is to prevent synthesis of specific enzymes in the pathway for ethylene biosynthesis. In one embodiment this invention relates to genetic alteration of coffee plants to eliminate synthesis of ACC synthase; in another, ACC oxidase synthesis is suppressed. In the presently preferred embodiments, synthesis of one or both of these enzymes is suppressed by transforming coffee plants with a DNA sequence that codes on transcription for a messenger RNA (mRNA) that is antisense to the mRNA that codes on expression for the enzyme whose synthesis is to be suppressed. See Oeller et al., Science 254:437 (1991), who reported controlling ripening of tomatoes using a similar strategy.

Recombinant DNA technology has been used to isolate a number of ACC synthase and ACC oxidase genes. However, the genes for ACC synthase and ACC oxidase in coffee have not been identified or sequenced to date.

SUMMARY OF INVENTION

The invention provides purified proteins, DNA sequences that code on expression therefore and recombinant DNA molecules, including hosts transformed therewith, for transforming coffee plants to suppress the expression of enzymes necessary for ethylene synthesis. The DNA sequences and recombinant DNA molecules are characerized in that they code on expression for the enzymes ACC synthase or ACC oxidase that are elements of the pathway for ethylene biosynthesis in coffee plants.

Coffee plants are transformed with vectors containing ACC synthase and/or with ACC oxidase DNA sequences inserted so that the transforming sequences code on expression for the respective RNA that is antisense to the mRNA for ACC synthase and/or ACC oxidase. The resulting antisense RNA binds to mRNA(s), thereby inactivating the mRNA encoding one or more enzymes in the pathway for ethylene synthesis. The described DNA sequences can also be used to block synthesis of ACC synthase or ACC oxidase using co-suppression. The result in either event is that the transformed plants are incapable of synthesizing ethylene, though other aspects of their metabolism is not affected.

Ripening in the transformed plants can be regulated by exogenous ethylene. By application of ethylene to the entire plant, the entire plant will ripen at once, making mechanical harvesting of coffee more productive.

SUMMARY OF THE DRAWINGS

FIG. 1 is the complete sequence of the cDNA encoding coffee fruit expressed ACC synthase.

FIG. 2 is the amino acid sequence of the coffee fruit ACC synthase deduced from the cDNA sequence shown in FIG. 1.

FIG. 3 is the sequence of the cDNA encoding coffee fruit expressed ACC oxidase.

FIG. 4 is the amino acid sequence of the coffee fruit ACC oxidase deduced from the cDNA sequence shown in FIG. 3.

DETAILED DESCRIPTION OF THE INVENTION

In order that the invention herein described may be more fully understood, the following detailed description is set forth. In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal, which also encodes the amino acid methionine ("MET").

Polypeptide—A linear array of amino acids connected one to the other by peptide bonds between the amino and carboxy groups of adjacent amino acids.

Genome—The entire DNA of a cell or a virus. It includes inter alia the structural gene coding for the polypeptides of the substance, as well as promoter, transcription and translation initiation and termination sites.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a gene or DNA sequence to produce a polypeptide. It is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (TETR) transforms a cell previously sensitive to tetracycline into one which is resistant to it. A cell transformed by a plasmid is called a "transformant."

Phage or Bacteriophage—Bacterial virus many of which consist of DNA sequences encapsidated in a protein envelope or coat ("capsid").

Cloning Vehicle—A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

cDNA—A DNA strand complementary to an mRNA that codes for a particular polypeptide.

The strategy for controlling ethylene biosynthesis in coffee plants according to the present invention relates in the first instance to determination of the genes that code on expression for two enzymes in the ethylene pathway: ACC synthase and ACC oxidase. Transformation of wild type coffee plants with constructs containing either or both genes in an orientation that is antisense to the normal genes is expected to block synthesis of the respective enzymes. Messenger RNA transcribed under direction from the transforming sequence will bind to mRMA transcribed under direction from the normal sequence, thereby inactivating the normal message and precluding enzyme synthesis.

To isolate the DNA sequences that code on expression for ACC synthase and ACC oxidase in coffee, we screened a cDNA library produced from coffee plant tissue with synthetic DNA probes containing nucleotide sequences expected to occur. These expected sequences were based on studies of nucleotide sequences that occur in genes that encode the respective enzymes, other climacteric plants and other plants.

In the present invention the cDNA corresponding to the gene encoding ACC synthase or ACC oxidase is used to transform embryonic coffee plants. The plasmid pBI-121 is used as a transforming vector. The sequences corresponding to DNA that codes on expression for ACC synthase or ACC oxidase is inserted into the plasmid in an inverted orientation adjacent to a cauliflower mosaic virus 35S promoter. RNA transcribed therefrom will be complementary to mRNA that encodes the amino acid sequence of the respective enzyme. Complete constructs are amplified in bacterial hosts. The hosts are disrupted and the amplified vector is attached to colloidal gold particles. The gold particles with adherent vectors are inserted into coffee plant tissue by propelling the particles at high speed at the cells as described in U.S. Pat. No. 5,107,065. Young plants successfully transformed are identified by antibiotic resistance. The transformed plants do not produce ACC synthase or ACC oxidase, depending on the gene used to transform the plants. Ripening of the transformed plants is initiated by application of exogenous ethylene.

EXAMPLE 1

Isolation of Coffee Fruit-Specific ACC Synthase cDNA

In order to isolate ACC synthase gene sequences involved in the ripening of coffee, a cDNA library was prepared from a mixture of coffee fruit pericarp and mesocarp tissue at different stages of ripeness. This library was screened using a PCR product synthesized from first-strand cDNA made from the same mRNA used to construct the library and degenerate oligonucleotide primers corresponding to consensus sequences derived from ACC synthase genes from other organisms. This example principally involved the isolation of mRNA, the construction of a cDNA library, and the subsequent steps involved in cloning the appropriate cDNA.

a) Isolation of mRNA

Total RNA was isolated from 66 g of pericarp and mesocarp tissue from several different developmental stages of coffee fruit (*C. arabica* L. cv Guatemalan) using the method of Levi et. al., [Hort Science 27(12):1316–1318 (1992)]. Frozen coffee fruit pericarp and mesocarp tissue was powdered by grinding for about 2 minutes in a domestic coffee mill (Salton Model GC-5; Salton Maxam Housewares Group, Mt. Prospect, Ill.) with a small piece of dry ice. The powdered fruit tissue was added to 200 mL of 200 mM tris[hydroxymethyl]aminomethane hydrochloride (tris-HCl) (pH 8.5), 1.5% sodium dodecyl sulfate (SDS), 300 mM LiCl, 10 mM disodium ethylenediaminetetraacetic acid ($Na_2EDTA$), 1.5% sodium deoxycholate (w:v), 1.5% Nonidet P-40 (Sigma Chemical Co.) (v:v), 0.5 mM thiourea, 1 mM aurintricarboxylic acid, 10 mM dithiothreitol (DTT), 75 mM β-mercaptoethanol, 2% polyvinylpyrrolidone (PVP) and 2% polyvinylpoly-pyrrolidone (PVPP) and homogenized using a Polytron tissue homogenizer (Tekmar, Cincinnati, Ohio). After 2 minutes of homogenization, 200 mL of chloroform was added and homogenization continued for a further 3 minutes. The homogenate was transferred to 250 mL centrifuge bottles (Nalgene) and centrifuged for 15 minutes at 2,500×g. The upper aqueous phase was removed and mixed with 12 mL of 5M NaCl, equally divided into two centrifuge bottles, and 150 mL of ethanol was added to each bottle. The mixture was stored at −20° C. overnight. The RNA was collected by centrifugation at 4,000×g for 15 minutes at 4° C. The RNA was dissolved in 50 mL TE1 (50 mM tris-HCL [pH 8.0], 10 mM $Na_2EDTA$) and clarified by centrifugation at 12,000×g for 10 minutes at 4° C. The supernatant was transferred to a new centrifuge bottle and 3 mL of 5M NaCl and 30 mL of isopropanol were added. The contents were mixed and stored at −20° C. overnight. The RNA was collected by centrifugation at 14,000×g for 10 minutes. The RNA was washed with 20 mL of 70% ice-cold ethanol and collected by centrifugation as before. After drying under vacuum for 10 minutes, the RNA was resuspended in 50 mL of TE1 buffer and 10 mL of 12M LiCl was added. The solution was incubated at 4° C. for 48 hours and the RNA was collected by centrifugation at 14,000×g for 10 minutes and resuspended in 30 mL TE1 buffer. After the addition of 15 mL of 5M potassium acetate, the RNA was incubated overnight at 0° C., recovered by centrifugation at 14,000×g for 10 minutes and suspended in 50 mL TE1 buffer. Three mL of 5M NaCl and 110 mL of 95% ethanol were added and the RNA was incubated at −20° C. overnight. The RNA was recovered by centrifugation at 14,000×g for 10 minutes, washed with 20 mL of 70% ice-cold ethanol, recovered by centrifugation as above, dried under vacuum for 10 minutes and resuspended in 600 μL of TE1 buffer. The RNA was transferred into a microcentrifuge tube and centrifuged at 14,000 rpm for 30 minutes at 4° C. after which 300 μL was removed to each of two new microcentrifuge tubes. The original centrifuged tube was rinsed with an additional 300 μL of TE1 buffer. Eighteen μL of 5M NaCl and 636 μL of 100% ethanol were added to each of the three tubes. After mixing by inverting, the tubes were stored overnight at −20° C. The RNA was collected by centrifugation at 14,000 rpm for 30 minutes and washed with 1 mL of 70% ice-cold ethanol. After centrifugation and drying as above, the RNA was resuspended in 400 μL sterile $H_2O$. A total of 1.04 mg total RNA was obtained.

Messenger RNA (polyA$^+$ RNA) was isolated using the PolyATtract® mRNA Isolation System IV (Promega Corporation, Madison, Wis.). A total of two isolations were done as follows. For each isolation, 0.48 mg total RNA was dissolved in 800 μL of RNase-free water. After heating at 65° C. for 10 minutes, 3 μL of 50 pmole/mL biotinylated oligo(dT) and 20.7 μL of 20× SSC (1× SSC contains 150 mM NaCl and 15 mM sodium citrate) were added and the mixture was allowed to slowly cool to room temperature over a period of approximately 30 minutes. An aliquot of streptavidin paramagnetic particles (provided in the PolyATtrack® mRNA Isolation System IV) was washed 3 times in 0.5× SSC and resuspended in 0.1 mL of 0.5× SSC. The RNA solution containing the biotinylated oligo(dT) was added to the washed streptavidin paramagnetic particles. After a 10 minute incubation at room temperature, the paramagnetic particles containing the trapped mRNA were captured to the side of the tube using a magnet.

The supernatant was removed and the particles were washed four times with 0.3 mL of 0.1× SSC. The mRNA was removed from the biotinylated oligo(dT) particles by suspending in 200 μL RNase-free water. An additional elution was carried out by adding 150 μL of water sequentially to each of the two tubes. The elution fractions (550 μL) were pooled and centrifuged at 14,000 rpm in a microcentrifuge for 30 minutes at 4° C. The supernatant was divided into two microcentrifuge tubes and, after the addition of ⅒th volume of 3M NaCl and 600 μL of ethanol, the mRNA was recovered by incubating the tubes at −20° C. overnight, followed by centrifugation as above. The mRNA was washed once with 1 mL of ice-cold 70% ethanol, dried and resuspended in 20 μL sterile $H_2O$. One μL was added to 1 mL of water and a spectrum was obtained from 230 nm through 330 nm in a Shimadzu UV 160U spectrophotometer. Approximately 6 μg of mRNA was recovered from 1.04 mg of total RNA.

b) Construction of a cDNA Library

First and second strand cDNA was synthesized using the ZAP-cDNA synthesis kit (Stratagene, La Jolla, Calif.). Six micrograms of mRNA in 20 μL of water were incubated at 65° C. for 5 minutes. Two microliters of 100 mM methyl mercury were added and incubation was continued at room temperature for 10 minutes. Four microliters of 700 mM β-mercaptoethanol were added and the incubation was continued for an additional 5 minutes. To the denatured mRNA, 5 μL of 10× first strand buffer (provided in the kit), 5 μL of 100 mM DTfT, 3 μL nucleotide mixture (10 mM each dATP, dGTP, dTTP and 5-methyl-dCTP), 2 μL of 1.4 μg/μL linker-primer:

5'-GAGAGAGAGAGAGAGAGAGAACTAGTCTCG
 AGTTTTTTTTTTTTTTTTTT-3' (SEQ. ID NO. 1)

1 μL RNase block and 5 μL of water were added. The reaction was incubated at room temperature for 10 minutes to anneal the primer to the mRNA and then 3 μL of 20 U/μL M-MuLV reverse transcriptase were added. Five microliters of this reaction mixture were removed to a tube containing 0.5 μL (0.625 pmoles) of 800 Ci/mmole [α-$^{32}$P]dATP. Both reactions were incubated at 37° C. for 1 hour. The radioactively labeled reaction was frozen at −20° C. for later gel analysis. To the 45 μL main reaction, 40 μL of second strand buffer, 15 μL of 100 mM DTT, 6 μL of nucleotide mixture (10 mM dATP, dGTP, dTTP and 26 mM dCTP), 268.3 μL water and 2 μL (2.5 pmoles) of 800 Ci/mmol [α-$^{32}$P]dATP were added. After mixing, 4.5 μL of 1 U/μL RNase H and 19.2 μL of 5.2 U/μL *E. coli* DNA polymerase I were added and the reaction was incubated at 16° C. for 2.5 hours. The reaction was extracted with 400 μL of phenol:chloroform (1:1). The phases were separated by centrifugation in a microcentrifuge for 5 min and the aqueous phase removed and re-extracted with chloroform. The aqueous phase was recovered by centrifugation as before.

The double-stranded cDNA was precipitated by the addition of 33.3 μL of 3M sodium acetate (pH 5.2) and 867 μL of 100% ethanol and incubation overnight at −20° C. The cDNA was recovered by centrifugation at 14,000×g in a microcentrifuge at 4° C. for 60 minutes. The cDNA was washed with 1 mL of 80% ethanol, recovered by centrifugation at room temperature in a microcentrifuge at 14,000× g, dried under vacuum and dissolved in 45 µL of water. Three microliters of the resuspended double-stranded cDNA was removed and stored at −20° C. for later analysis by gel electrophoresis.

To the remaining 42 µL of the double-stranded cDNA, 5 µL of 10× Klenow buffer (buffer #3; supplied by Stratagene), 2.5 µL of 2.5 mM nucleotides (dCTP, dGTP, dATP and DTTP), and 0.5 µL of 5 U/µL E. coli DNA polymerase I Klenow fragment were added. After 30 minutes at 37° C., 50 µL of water were added and the reaction was extracted with an equal volume of phenol:chloroform (1:1) and then chloroform as described above. After the addition of 7 µL of 3M sodium acetate (pH 5.2) and 226 µL of 100% ethanol, the blunt-ended double-stranded cDNA was incubated on ice for 30 minutes and recovered by centrifuging at 14,000 rpm at 4° C. for 60 minutes in a microcentrifuge. The cDNA was washed with 300 µL of 70% ethanol, centrifuged and dried as before. Seven microliters of 0.4 µg/µL EcoRI linkers were added to the dried cDNA. The structure of the EcoRI linkers are:

5'-AATTCGGCACGAG-3' (SEQ. ID NO. 2)
3'-GCCGTGCTC-5'

After vortexing to resuspend the cDNA, 1 µL of 10× ligation buffer, 1 µL 10 mM ATP and 1 µL of 4 Weiss U/µL T4 DNA ligase were added and the reaction was incubated over night at 8° C. The ligase was inactivated by heating at 70° C. for 30 minutes. The 5' ends of the EcoRI linkers, that are now attached to the cDNA, were phosphorylated using polynucleotide kinase. One microliter of 10× buffer #3 of the ZAP-cDNA synthesis kit (Stratagene, La Jolla, Calif.), 2 µL of 10 mM ATP, 6 µL of water and 1 µL of 10 U/µL T4 polynucleotide kinase were added to the ligation reaction. After 30 minutes at 37° C. the kinase reaction was stopped by heating the reaction at 70° C. for 30 minutes. XhoI "sticky ends" were generated at the end of the cDNA corresponding to the 3' end of the mRNA by digestion of the XhoI site in the linker-primer. Twenty-eight µL of XhoI buffer and 3 µL of 40 U/µL XhoI were added to the cDNA and the reaction was incubated at 37° C. for 1.5 hours.

The cDNA, with EcoRI sticky ends at the 5' end and XhoI sticky ends at the 3' end (relative to the original mRNA), was size fractionated by passage through a Sephacryl S-400 spin column prepared as follows. Five µL of 10× STE [100 mM Tris (pH 7.0), 5 mM EDTA and 100 mM NaCl] were added to the cDNA and the cDNA was applied to the top of a 1 mL syringe containing Sephacryl S-400 (Pharmacia Biotech, Piscataway, N.J.). A 500 µL microcentrifuge tube was placed on the bottom of the syringe and the column was placed in a centrifuge tube and centrifuged at about 400×g for 2 minutes. Sixty µL of 1× STE were added to the top of the syringe, a new microcentrifuge tube was placed on the bottom of the column and the column was again centrifuged as before. This process was repeated until six fractions had been collected. About 10% of each fraction was electrophoresed on a 1% agarose gel to determine the size distribution of the cDNA in each fraction. The remainder of each fraction was extracted with an equal volume of phenol:chloroform and then chloroform as described above and precipitated by the addition of 2 volumes of 100% ethanol. After overnight incubation at −20° C. the cDNA was recovered by centrifugation in a microcentrifuge at 14,000 rpm for 60 minutes at 4° C. Each cDNA fraction was washed with 200 µL of 80% ethanol and dried as described above. cDNA fraction 1 was resuspended in 3 µL of sterile water, and cDNA fraction 2 was resuspended in 10.5 µL of sterile water. One-half µL of each of the two fractions was used to determine the quantity of DNA using the ethidium bromide plate detection method. Fractions 1 and 2, containing the largest cDNA molecules, were combined. The 12.5 mL combined fractions contained approximately 100 ng of cDNA. This fraction was reduced to 2.5 µL in a Speed-Vac and stored on ice. cDNA fraction 3 was resuspended in 10.5 µL of sterile water, and saved at −20° C. for later use.

One-hundred ng of cDNA from fraction 1 and 2 were ligated into 1 µg of Uni-ZAP™ (Stratagene, La Jolla, Calif.), a lambda ZAP vector that had been digested with EcoRI and XhoI. Fraction 1 and 2 cDNA (2.5/µL) were added to 0.5 µL of 10 X ligation buffer, 0.5 µL 10 mM ATP, 1 µL of 1 µg/µL Uni-Zap XR vector and 0.5 µL of 4 Weiss U/µL T4 DNA ligase. The reaction was incubated at 8° C. for about 44 hours. A 1 µL aliquot of the ligation reaction was added to one aliquot of the 'Freeze-Thaw' extract from the Gigapack II Gold bacteriophage λ packaging kit (Stratagene, La Jolla, Calif.). Fifteen microliters of Sonic extract were added and the contents were gently mixed. The packaging was carried out at room temperature. After 2 hours, 500 µL of SM buffer and 20 µL of chloroform were added to each packaging reaction and the debris was removed by a short centrifugation in a microcentrifuge. The packaged phages were moved to a new microcentrifuge tube. Ten µL of chloroform were added and the packages phages were stored at 4° C. until used. A titer of this primary library indicated the presence of $0.7 \times 10^6$ recombinant plaques.

c) Amplification of primary library.

Six-hundred µL of E. coli XL1-Blue MRF' (Stratagene, La Jolla, Calif.), grown to a density of 0.5 at O.D.$_{600}$, and 32.5 µL of primary library stock were added to each of 16 tubes. After incubation at 37° C. for 15 min, 6.0 mL of 48° C. top agar (5 g/L NaCl, 2 g/L MgSO$_4$. 7H$_2$O, 5 g/L yeast extract, 10 g/L NZ amine [pH 7.5], and 0.7% agarose) were added to each tube and the contents were plated on 150×15 mm NZY plates (5 g/L NaCl, 2 g/L MgSO$_4$. 7H$_2$O, 5 g/L yeast extract, 10 g/L NZ amine [pH 7.5], and 15 g/L Difco agar). The plates were incubated overnight at 37° C. and then overlayed with 10 mL of SM buffer and incubated for a further 8 hours at 4° C. with gentle shaking. The SM buffer was collected with a sterile pipette and stored in a sterile 250 mL centrifuge bottle. Each plate was rinsed with an additional 10 mL of SM buffer which were collected and added to the previous SM buffer. Chloroform, to a final concentration of 5%, was added and the phage solution was incubated at room temperature for 15 minutes and then centrifuged at 2,000×g for 10 minutes to remove cell debris. The supernatant was recovered to a sterile polypropylene bottle and chloroform was added to a final concentration of 0.3%. The amplified library was stored at 4° C.

d) Plating of amplified library for screening for specific genes.

The amplified library was titered as described above. Approximately 50,000 recombinant plaques were added to 600 µL of E. coli XL1-Blue MRF' that were grown as described above. After 15 min at 37° C., 6.5 mL of 48° C. top agar were added and the cells were plated on 150×15 mm NZY plates. Four plates containing a total of 200,000 recombinant plaques were prepared and incubated at 37° C. overnight. The plates were then chilled for 4 hours at 4° C., then used for preparing plaque lifts as described below.

e) Identification and Construction of Oligonucleotides Homologous to Coffee ACC Synthase Genes In previous studies, described in United States patent application Ser. No. 08/485,107 the specification of which has been incorporated herein by reference, we identified base sequences common to ACC synthase occurring in a variety of plants, referred to herein as consensus sequences. Based on these studies, we developed a set of three (3) fully degenerate primers for PCR amplification of regions of coffee first strand cDNA corresponding to consensus sequences. The sequence of the primers used is:

ACS167: 5'-GCCAAGCTTCCRTGRTARTCYTGRAA-3' (SEQ. ID NO. 3)

ACS289: 5'-TTYCARGAYTAYCAYGGHYT-3' (SEQ. ID NO. 4)

ACS885: 5'-CCHGGDARNCCYAWRTCTTT-3' (SEQ. ID NO. 5)

f) Reverse Transcriptase reaction to obtain first-strand coffee cDNA.

The reverse transcriptase reaction to obtain first-strand cDNA was performed in a final volume of 20 μL using the GeneAmp RNA PCR Core Kit (Perkin Elmer, Foster City, Calif.). First, 0.9 μg of coffee fruit mRNA in 3 μL water was mixed with 1 μL of 50 μM random hexamer and 6 μL of sterile water in a microcentrifuge tube and incubated at 65° C. for 5 minutes. The mixture was left at room temperature for 2 minutes and the liquid was recovered to the bottom of the tube by a brief centrifugation. To this mixture 2 μL PCR buffer II (from the above mentioned kit), 4 μL 25 mM $MgCl_2$, 2 μL 10 mM dNTP's, 1 μL RNAsin (20 u/μL), and 1 μL reverse transcriptase (50 u/μL) were added. The reaction was incubated at 42° C. for 1 hour after which the reverse transcriptase was heat inactivated in a 95° C. water bath for 5 minutes.

g) Polymerase chain reaction to amplify coffee ACC-synthase gene.

A polymerase chain reaction (PCR) (Saiki et al., 1988) was performed using the GeneAmp Kit described above in a 50 μL reaction containing 10 μL first-strand cDNA mix, 4 μL PCR buffer II, 1 μL 25 mM $MgCl_2$, 2.5 μL of 20 μM ACS167 primer (SEQ. ID NO. 3), 2.5 μL 20 μM ACS885 primer (SEQ. ID. NO. 5), 29.5 μL sterile $H_2O$, and 0.5 μL Taq DNA polymerase (5 u/μL). PCR conditions were 35 cycles of 94° C. for 1 minute, 44° C for 1 minute, and 72° C. for 2 minutes. The product of the PCR reaction was analyzed by agarose gel electrophoresis using 1.5% Sea-Plaque agarose (FMC BioProducts, Rockland, Me.) and Hae III-digested φX174 DNA (Promega Corporation, Madison, Wis.) as size markers. A single PCR product of approximately 650 bp was obtained.

h) Amplification of PCR product with different primers.

The 650 bp fragment obtained above was excised from the gel and placed in a 1.5 mL microcentrifuge tube. After the addition of 200 μL of sterile water, the 650 bp fragment was heated to 90° C. for 5 minutes, cooled to room temperature and centrifuged at 14,000 rpm for 5 minutes in a microcentrifuge. The supernatant containing the amplified DNA was removed and placed in a new sterile 1.5 mL microcentrifuge tube. A 25 μL PCR reaction was carried out using 0.4 μL of the previously amplified DNA as template, 2.5 μL 10× PCR buffer (10 mM Tris-HCl pH 9.0, 0.1% triton X-100), 2 μL 25 mM $MgCl_2$, 5 μL of 1 mM dNTPs, 1 μL of 20 μM ACS289 primer (SEQ. ID. NO. 4), 1 μL of 20 μM ACS885 primer (SEQ. ID. NO. 5), 12.8 μL $H_2O$, and 0.3 μL Taq DNA polymerase (5 u/μL)(Promega Corporation, Madison, Wis.). The PCR was performed using 35 cycles of 94° C. for 1 minute, 45° C. for 1 minute, and 72° C. for 2 minutes Five μL of this reaction was electrophoresed in a 1.5% agarose gel as described above. A single product of approximately 603 bp was observed. Eighty μL of sterile water, 10 μL of 3M sodium acetate (pH 5.2), and 220 μL of 100% ethanol was added to the remainder of the reaction. After incubation at −20° C. overnight, the DNA was recovered by centrifugation at 4° C. for 30 minutes at 14,000 rpm. The DNA was washed with 400 μL of ice-cold 75% ethanol and resuspended in 25 μL of sterile water. The DNA concentration was determined to be 10 ng/μL using the ethidium bromide plate assay.

i) Labeling Coffee Fruit-Specific ACC Synthase DNA

A random primed probe was produced using the PCR-generated ACC synthase DNA and the Prime-a-Gene Kit (Promega Corporation, Madison, Wis.). Two and one-half μL of the DNA (25 ng) was added to 27.5 μL of sterile water and the DNA was denatured by boiling for 5 min. Ten μL of 5× labeling buffer, 2 μL of unlabeled dNTP's [20 μM each; dCTP, dGTP, dTTP], 2 μL 1 mg/mL acetylated BSA, 1 μL 5u/μL E. coli DNA polymerase I Klenow fragment and 5 μL (50 μCi) of [α-$^{32}$P]dATP (3,000 Ci/mmole) (Dupont-NEN) were added to give a final volume of 50 μL. After 1 hr at room temperature, the reaction was terminated by the addition of 2 μL of 0.5M $Na_2EDTA$ and boiling for 2 min.

j) Screening of amplified library with the ACC synthase-specific probe.

Plaque lifts of the four 150×15 mm NZY plates containing 50,000 recombinant clones each were prepared. Four 132 mm Magna nylon transfer membranes (Micron Separations, Incorporated, Westborough, Mass.) were wetted by placing them on chromatography paper saturated with 5× SSC buffer for approximately 10 sec. The membranes were placed on the plates containing the recombinant plaques for 5 min, removed and incubated, phage containing side up, for 2 min on chromatography paper saturated with 0.5M NaOH and 1.5M NaCl. The membranes were then neutralized by transferring onto chromatography paper saturated with 0.5 M tris-HCl (pH 8.0) and 1.5M NaCl, for 5 min. After a brief 20 sec treatment on chromatography sheets saturated with 2× SCC containing 0.2M Tris-HCl (pH 7.5), the filters were blotted dry. After 1 hour of air drying, DNA was cross-linked to the membranes by treatment with 12,000 μJoules of a 260 nm UV light in a UV Stratalinker 1800 (Stratagene, La Jolla, Calif.).

The four membranes were prehybridized at 65° C. for 2 hours in 100 mL 6× SSPE (52.2 g/L NaCl, 8.3 g/L $NaH_2PO_4.H_2O$, 2.2 g/L $Na_2EDTA$, [pH 7.4]), 5× Denhardt's solution (1 g/L Ficoll, 1 g/L polyvinylpyrrolidone, 1 g/L BSA [pentax fraction V]), 0.5% SDS and 100 μg/mL denatured herring sperm DNA in a Hybaid Mark II hybridization oven (National Labnet Company, Woodbridge, N.J.) using HB-OV-BL bottles.

Hybridization was carried out at 65° C. for 12 hours in 10 mL of 6× SSPE containing 0.5% SDS, 100 μg/mL denatured herring sperm DNA, and 52 μL of the random primed probe described above. At the end of the hybridization period the hybridization solution was removed and the membranes were briefly washed with 100 mL of 2× SSC containing 0.5% SDS at 65° C. They were then washed for an additional 30 min with the same amount of fresh buffer again at 65° C. The membranes were washed twice more for 30 min at 65° C. with 100 mL of 0.2× SSC containing 0.5% SDS, wrapped in a cellophane envelope and exposed to pre-flashed Fuji $RX_{GCU}$ X-ray film at −70° C. for 24 hours. Ten positive clones were obtained. The region of the original plates corresponding to the identified plaques were removed and placed in 1 mL of SM buffer containing 20 μL chloroform.

Of these ten, 5 were re-plated at lower densities and rescreened as above to obtain individual plaques.

k) Characterization of Coffee-Fruit ACC synthase cDNA clones.

The size of the putative coffee ACC synthase cDNA clones was determined by polymerase chain reaction using primers homologous to a portion of the T3 and T7 promoters present in the cloning vector and flanking the cDNA insertion site. The sequence of the primers are:

T3: 5'-TAATACGACTCACTATAGGG-3' (SEQ. ID NO. 6)

T7: 5'-AATTAACCCTCACTAAAGGG-3' (SEQ. ID NO. 7)

The conditions for PCR were as described above except that the temperature cycle was 95° C. for 1 min., 50° C. for 1 min. and 72° C. for 2 min. Analysis was by agarose gel electrophoresis as before.

The three largest clones were recovered as phagemids by in vivo excision. Two hundred μL of phage stock from a single plaque was mixed with 200 μL of E. coli XL1-Blue MRF' grown to a density at $O.D._{600}$ of 1.0. One μL of ExAssist (Stratagene, La Jolla, Calif.) helper phage (>1×10$^6$ pfu/μL) was added and the tubes were incubated at 37° C. for 15 min. Three mL of sterile LB broth were added and they were incubated for 3 hours at 37° C. with shaking. After heating at 70° C. for 20 min and centrifugation at 1,000×g for 15 min, 1 mL of the supernatant, containing the excised pBluescript phagemid packaged as filamentous phage particles, was transferred to a sterile 1.5 mL microcentrifuge tube and stored at 4° C. Phagemids were recovered by adding 25 μL of the stock solution to 200 μL of E. coli Solar cells (Stratagene, La Jolla, Calif.) grown to a density of 1 when measured at $O.D._{600}$. After incubation at 37° C. for 15 min, 200 μL of the cell mixture was plated on 100×15 mm NZY agar plates containing 50 μg/mL ampicillin. The plates were incubated overnight at 37° C. Individual colonies were picked into 10 mL of LB broth containing 50 μg/mL ampicillin and grown overnight in a 37° C. shaking incubator. The cells were concentrated in a 1.5 mL sterile microcentrifuge tube by repeated centrifugation and the phagemid DNA was purified using the plasmid mini kit from QIAGEN. The bacterial pellets were washed with water and resuspended in 0.3 mL of buffer P1. Next, 0.3 mL of alkaline lysis buffer P2 was added, mixed gently, and incubated for less than 5 min at room temperature. Following the addition of 0.3 mL of chilled buffer P3 and mixing by inverting the tubes 6 times, the extracts were incubated on ice for 10 min and centrifuged at 14,000 rpm for 15 min in a microcentrifuge. The supernatants were removed and applied to QIAGEN-tip 20 columns that had been previously equilibrated with 1 mL of QDT buffer. The extracts were allowed to enter the resin of the columns by gravity flow. Once the flow had stopped, the columns were washed 4 times with 1 mL buffer QC. The DNAs were eluted by washing the QIAGEN-tip 20 columns with 0.8 mL buffer QF which was collected into 1.5 mL microcentrifuge tubes. The DNA was precipitated by the addition of 0.7 volumes (560 μL) of isopropanol. The tubes were immediately centrifuged at 14,000 rpm for 30 min and the supernatant carefully removed. The pellets, containing the DNA, were washed with 1 mL of ice-cold 70% ethanol, centrifuged as above, and air dried for 5 min. The DNA was resuspended in 50 μL sterile $H_2O$. The concentration of DNA from one plasmid isolation was 0.1 μg/μL by fluormetric analysis.

Sequencing reactions were performed by mixing 8 μL of phagemid DNA (0.8 μg) with 4 μL of either T3 or T7 sequencing primers (0.8 pmol/μL). Automated DNA sequencing was carried out on these samples at the University of Hawaii Biotechnology Service Center. About 350 bp of sequence from both the 5' and the 3' end of the cDNA was obtained. New sequencing primers were synthesized based on sequences near the end of the previous sequences and used in the same manner to complete the sequence of both strands of the cDNA. The complete sequence of the coffee fruit-expressed ACC synthase cDNA is given in FIG. 1 and SEQ ID NO: 11. The deduced amino acid sequence of the coffee fruit-expressed ACC synthase is given in FIG. 2 and SEQ ID NO: 10.

The sequence of the coffee ACC synthase cDNA clone and deduced protein was compared with other ACC synthase genes present in GenBank. The cDNA isolated from coffee fruit shows from 68.3% to 58.1% identity to other ACC synthases present in GenBank. And, the protein sequence deduced from this cDNA shows from 67.9% to 50.5% identity to other ACC synthases. However, this cDNA is unique in that no other sequence greater than 1500 bp showed greater than 68.3% identity to it.

EXAMPLE 2

Isolation of Coffee Fruit-Specific ACC Oxidase a) Synthesis of ACC Oxidase specific oligonucleotide primers.

The isolation of total RNA, mRNA, and the synthesis of coffee fruit-specific cDNA was as described above.

Twelve ACC oxidase sequences, obtained from GenBank, were aligned using the Pileup program of GCG (Genetics Computer Group, Madison, Wis.). A region approximately 1000 bp from the translation start codon was found to be conserved and a degenerate oligonucleotide primer

5'-TCATIGCKKCRAKIGGTTC-3' (SEQ. ID NO. 8)

corresponding to this region was synthesized. Inosine (I) was placed at positions showing no sequence conservation, since position could be any of A, T, G or C. Positions showing two-fold ambiguity were prepared with mixed residues (T/G or A/G). We also prepared a second primer homologous to a region of the papaya fruit-expressed ACC oxidase cDNA that had been previously cloned in our laboratory and situated approximately 372 bp from the translational start codon:

5'-GACACTGTGGAGAGGCTGAC-3' (SEQ. ID NO. 9)

The two primers were used in a PCR reaction to amplify a portion of the coffee fruit-expressed ACC oxidase cDNA. The PCR contained 0.2 μL (10 ng) cDNA fraction 3 (described in Example 1), 5 μL 10× PCR buffer, 3 μL 25 mM $MgCl_2$, 1 μL of each of the four 10 mM dNTPs, 1 μL of a 20 μM solution of each primer, 0.3 μL Taq DNA polymerase (Promega Corporation, Madison, Wis.) and 38.5 μL water. PCR conditions were 35 cycles of 94° C. for 1 min, 50° C. for 1 min, and 72° C. for 1 min. A 5 min incubation at 72° C. was carried out after the last cycle. A 20 μL aliquot of the product was electrophoresed in a 1.5% agarose gel as described previously and revealed an approximately 800 bp product. The DNA was excised from the gel and mixed with 200 μL of sterile water in a 1.5 mL microcentrifuge tube. After boiling for 5 min, 2 μL was used as a template in a 50 μL PCR reaction as above using the same primers. Gel electrophoresis performed as described above using 20 μL of the PCR reaction indicated the presence of a single 800 bp product. To the remaining 30 μL of the PCR reaction 20 μL chloroform and 100 μL water was added. The contents were mixed and centrifuged for 2 minutes at 14,000 rpm in a microcentrifuge. The upper aqueous phase containing the DNA was removed to a clean microcentrifuge tube. A portion of this DNA was radioactively labeled by random primed synthesis as described above.

13 b) Screening of amplified library with random primed probe.

The amplified coffee-fruit cDNA described in Example 1 was used to prepare four 150×10 mm NZY plates as previously described. Prehybridization, hybridization and recovery of clones was as previously described except that the ACC oxidase sequence obtained by PCR was used as the probe.

c) Characterization of Coffee-Fruit ACC-oxidase cDNA clones.

The size of the coffee ACC-oxidase cDNA clones was determined by polymerase chain reaction using primers homologous to the T3 and T7 promoters as described in Example 1.

14

The sequence of the largest coffee ACC oxidase cDNA clone was obtained as described in Example 1 and compared with ACC oxidase genes present in GenBank. FIG. 3 and SEQ ID NO: 13 give the sequence of the coffee fruit-specific ACC oxidase. FIG. 4 and SEQ ID NO: 12 give the deduced amino acid sequence of this protein. The cDNA was determined to encode ACC oxidase because it is from 50.4% to 82.5% identical to other ACC synthases nucleic acid sequences present in GenBank. Also, the deduced protein sequence is from 32.5% to 86.5% identical to other ACC oxidases.

The foregoing examples are for illustrative purposes only, and should not be viewed as limiting the scope of applicants' invention, which is set forth in the claims appended hereto.

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 15 amino acid residues
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Fragment A
        ( B ) LOCATION: 17..1480

( x i ) SEQUENCE DESCRIPTION: SEQ ID NO:1:

```
Ile  Asn  Tyr  Ala  Ser  Gly  Ala  Ser  Gly  Ile  Leu  Asp  Gln  Xaa  Gly
 1              5                        10                      15
```

( 2 ) INFORMATION FOR SEQ ID NO:2:

( i ) SEQUENCE CHARACTERISTICS:
        ( A ) LENGTH: 14 amino acid residues
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Ile  Asn  Tyr  Ala  Ser  Gly  Ala  Ser  Gly  Ile  Leu  Asp  Gln  Thr
 1              5                        10                      14
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: OTHER NUCLEIC ACID
        ( A ) DESCRIPTION: PRIMER ( v ) FRAGMENT TYPE: Internal ( i x ) FEATURE:
        ( A ) OTHER INFORMATION: N IS INOSINE ( x i ) SEQUENCE DESCRIPTION: SEQ ID NO:3:

ATNAAYTAYG CNAGYGGNGC        20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: OTHER NUCLEAR ACID
        ( A ) DESCRIPTION: PRIMER ( v ) FRAGMENT TYPE: INTERNAL ( i x ) FEATURE:
        ( A ) OTHER INFORMATION: N IS INOSINE ( x i ) SEQUENCE DESCRIPTION: SEQ ID NO:4:

ATNAAYTAYG CNAGYGGNGC                                              20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: OTHER NUCLEIC ACID
        ( A ) DESCRIPTION: PRIMER ( v ) FRAGMENT TYPE: INTERNAL ( i x ) FEATURE:
        ( A ) OTHER INFORMATION: N IS INOSINE ( x i ) SEQUENCE DESCRIPTION: SEQ ID NO:5:

CGNCCAGNCG NYTAYTTNAT                                              20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)
        ( A ) DESCRIPTION: PRIMER ( v ) FRAGMENT TYPE: INTERNAL ( i x ) FEATURE:
        ( A ) OTHER INFORMATION: N IS INOSINE ( x i ) SEQUENCE DESCRIPTION: SEQ ID NO:6:

CGNCCYCTYG CYTAYTTNAT                                              20

( 2 ) INFORMATION FOR SEQ ID NO:7:

( i ) SEQUENCE CHARACTERISTICS:
        ( A ) LENGTH: 14 amino acid residues
        ( B ) TYPE: amino acid
        ( C ) STRANDEDNESS: single
        ( D ) TOPOLOGY: linear ( i i ) MOLECULE TYPE: peptide ( v ) FRAGMENT TYPE: INTERNAL ( i x ) FEATURE:
        ( D ) OTHER INFORMATION: Xaa is either Thr or Asp ( x i ) SEQUENCE DESCRIPTION: SEQ ID NO:7:

```
Gln  Tyr  Val  Pro  Cys  Tyr  Phe  Xaa  Phe  Ile  Asp  Asp  Gln  Asp
 1              5                        10                      14
```

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: OTHER NUCLEIC ACID
        ( A ) DESCRIPTION: PRIMER ( v ) FRAGMENT TYPE: Internal ( i x ) FEATURE:
        ( A ) OTHER INFORMATION: N IS INOSINE ( x i ) SEQUENCE DESCRIPTION: SEQ ID NO:8:

CAWTATGTNC CNTGTTATTT 20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: OTHER NUCLEIC ACID
        ( A ) DESCRIPTION: PRIMER ( v ) FRAGMENT TYPE: Internal ( i x ) FEATURE:
        ( A ) OTHER INFORMATION: N IS INOSINE ( x i ) SEQUENCE DESCRIPTION: SEQ ID NO:9:

AAWTAWCAHG GNACWTATTG 20

( 2 ) INFORMATION FOR SEQ ID NO:10:

( i ) SEQUENCE CHARACTERISTICS:
        ( A ) LENGTH: 488 amino acid residues
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY:CDS
        ( B ) LOCATION:178..1653

( x i ) SEQUENCE DESCRIPTION: SEQ ID NO:10:

```
Met  Glu  Phe  Ser  Leu  Lys  Asn  Glu  Gln  Gln  Gln  Leu  Leu  Ser  Lys
 1              5                        10                            15

Met  Ala  Thr  Asn  Asp  Gly  His  Gly  Glu  Asn  Ser  Pro  Tyr  Phe  Asp
                20                        25                            30

Gly  Trp  Lys  Ala  Tyr  Asp  Ser  Asp  Pro  Tyr  His  Pro  Thr  Arg  Asn
                      35                        40                      45

Pro  Asn  Gly  Val  Ile  Gln  Met  Gly  Leu  Ala  Glu  Asn  Gln  Leu  Cys
                      50                        55                      60

Phe  Asp  Leu  Ile  Glu  Glu  Trp  Val  Leu  Asn  Asn  Pro  Glu  Ala  Ser
                      65                        70                      75

Ile  Cys  Thr  Ala  Glu  Gly  Ala  Asn  Lys  Phe  Met  Glu  Val  Ala  Ile
```

|   |   |   |   |   | 80 |   |   |   |   | 85 |   |   |   |   | 90 |
|---|---|---|---|---|---|---|---|---|---|---|---|---|---|---|---|

Tyr Gln Asp Tyr His Gly Leu Pro Glu Phe Arg Asn Ala Val Ala
              95                    100                   105

Arg Phe Met Glu Lys Val Arg Gly Asp Arg Val Lys Phe Asp Pro
              110                   115                   120

Asn Arg Ile Val Met Ser Gly Gly Ala Thr Gly Ala His Glu Thr
              125                   130                   135

Leu Ala Phe Cys Leu Ala Asp Pro Glu Asp Ala Phe Leu Val Pro
              140                   145                   150

Thr Pro Tyr Tyr Pro Gly Phe Asp Arg Asp Leu Arg Trp Arg Thr
              155                   160                   165

Gly Met Gln Leu Leu Pro Ile Val Cys Arg Ser Ser Asn Asp Phe
              170                   175                   180

Lys Val Thr Lys Glu Ser Met Glu Ala Ala Tyr Gln Lys Ala Gln
              185                   190                   195

Glu Ala Asn Ile Arg Val Lys Gly Phe Leu Leu Asn Asn Pro Ser
              200                   205                   210

Asn Pro Leu Gly Thr Val Leu Asp Arg Glu Thr Leu Ile Asp Ile
              215                   220                   225

Val Thr Phe Ile Asn Asp Lys Asn Ile His Leu Ile Cys Asp Glu
              230                   235                   240

Ile Tyr Ser Ala Thr Val Phe Ser Gln Pro Glu Phe Ile Ser Ile
              245                   250                   255

Ser Glu Ile Ile Glu His Asp Val Gln Cys Asn Arg Asp Leu Ile
              260                   265                   270

His Leu Val Tyr Ser Leu Ser Lys Asp Leu Gly Phe Pro Gly Phe
              275                   280                   285

Arg Val Gly Ile Leu Tyr Ser Tyr Asn Asp Ala Val Val Ser Cys
              290                   295                   300

Ala Arg Lys Met Ser Ser Phe Gly Leu Val Ser Thr Gln Thr Gln
              305                   310                   315

His Leu Ile Ala Ser Met Leu Ser Asp Glu Ala Phe Met Asp Lys
              320                   325                   330

Ile Ile Ser Thr Ser Ser Glu Arg Leu Ala Ala Arg His Gly Leu
              335                   340                   345

Phe Thr Arg Gly Leu Ala Gln Val Gly Ile Gly Thr Leu Lys Ser
              350                   355                   360

Ser Ala Gly Leu Tyr Phe Trp Met Asp Leu Arg Arg Leu Leu Arg
              365                   370                   375

Glu Ser Thr Phe Glu Ala Glu Met Glu Leu Trp Arg Ile Ile Ile
              380                   385                   390

His Glu Val Lys Leu Asn Val Ser Pro Gly Leu Ser Phe His Cys
              395                   400                   405

Ser Glu Pro Gly Trp Phe Arg Val Cys Phe Ala Asn Met Asp Asp
              410                   415                   420

Glu Ser Val Arg Val Ala Leu Arg Arg Ile His Lys Phe Val Leu
              425                   430                   435

Val Gln Gly Lys Ala Thr Glu Pro Thr Thr Pro Lys Ser Arg Cys
              440                   445                   450

Gly Ser Ser Lys Leu Gln Leu Ser Leu Ser Phe Arg Arg Leu Asp
              455                   460                   465

Glu Arg Val Met Gly Ser His Met Met Ser Pro His Ser Pro Met
              470                   475                   480

| Ala | Ser | Pro | Leu | Val | Arg | Ala | Thr |
|-----|-----|-----|-----|-----|-----|-----|-----|
|     |     |     |     | 485 |     |     |     |

( 2 ) INFORMATION FOR SEQ ID NO:11:

( i ) SEQUENCE CHARACTERISTICS:
        ( A ) LENGTH: 2040 base pairs
        ( B ) TYPE: nucleic acid
        ( C ) STRANDEDNESS: single
        ( D ) TOPOLOGY: linear ( i i ) MOLECULE TYPE: cDNA to mRNA ( i x ) FEATURE:
        ( A ) NAME/KEY:CDS
        ( B ) LOCATION:178..1653

( x i ) SEQUENCE DESCRIPTION: SEQ ID NO:11:

```
GTAATCTCTT  CTAAAATCAA  CCATTCTCTT  CATTCTTCAC  TTGACAAGGC           50

CACTGCATTC  TTCATTCTTT  CTTGATATAT  AGCCATTTTT  TTCATTCTTT          100

CTTGATATAT  AGCCATTTTT  TTCATTCTTT  CTTCATTCAT  TGTCTGGAGA          150

AGTTGGTTGA  GTTTCTTGA  AAATTCAAGC  AAAACA  ATG  GAG  TTC  AGT        198
                                           Met  Glu  Phe  Ser
                                            1
```

| TTG | AAA | AAC | GAA | CAA | CAA | CAA | CTC | TTG | TCG | AAG | ATG | GCA | ACC | 240 |
|-----|-----|-----|-----|-----|-----|-----|-----|-----|-----|-----|-----|-----|-----|-----|
| Leu | Lys | Asn | Glu | Gln | Gln | Gln | Leu | Leu | Ser | Lys | Met | Ala | Thr |     |
| 5   |     |     |     |  10 |     |     |     |     |  15 |     |     |     |     |     |

| AAC | GAT | GGA | CAT | GGC | GAA | AAC | TCG | CCT | TAT | TTT | GAT | GGT | TGG | 282 |
|-----|-----|-----|-----|-----|-----|-----|-----|-----|-----|-----|-----|-----|-----|-----|
| Asn | Asp | Gly | His | Gly | Glu | Asn | Ser | Pro | Tyr | Phe | Asp | Gly | Trp |     |
|     |  20 |     |     |     |  25 |     |     |     |     |  30 |     |     |     |     |

| AAG | GCA | TAT | GAT | AGT | GAT | CCT | TAC | CAT | CCC | ACC | AGA | AAT | CCT | 324 |
|-----|-----|-----|-----|-----|-----|-----|-----|-----|-----|-----|-----|-----|-----|-----|
| Lys | Ala | Tyr | Asp | Ser | Asp | Pro | Tyr | His | Pro | Thr | Arg | Asn | Pro |     |
|     |     |  35 |     |     |     |     |  40 |     |     |     |     |  45 |     |     |

| AAT | GGT | GTT | ATA | CAG | ATG | GGA | CTC | GCA | GAA | AAT | CAG | TTA | TGC | 366 |
|-----|-----|-----|-----|-----|-----|-----|-----|-----|-----|-----|-----|-----|-----|-----|
| Asn | Gly | Val | Ile | Gln | Met | Gly | Leu | Ala | Glu | Asn | Gln | Leu | Cys |     |
|     |     |     |  50 |     |     |     |     |  55 |     |     |     |     |  60 |     |

| TTT | GAT | TTG | ATC | GAG | GAA | TGG | GTT | CTG | AAC | AAT | CCA | GAG | GCT | 408 |
|-----|-----|-----|-----|-----|-----|-----|-----|-----|-----|-----|-----|-----|-----|-----|
| Phe | Asp | Leu | Ile | Glu | Glu | Trp | Val | Leu | Asn | Asn | Pro | Glu | Ala |     |
|     |     |     |     |  65 |     |     |     |     |  70 |     |     |     |     |     |

| TCC | ATT | TGC | ACA | GCA | GAA | GGA | GCG | AAC | AAA | TTC | ATG | GAA | GTT | 450 |
|-----|-----|-----|-----|-----|-----|-----|-----|-----|-----|-----|-----|-----|-----|-----|
| Ser | Ile | Cys | Thr | Ala | Glu | Gly | Ala | Asn | Lys | Phe | Met | Glu | Val |     |
|  75 |     |     |     |  80 |     |     |     |     |  85 |     |     |     |     |     |

| GCT | ATC | TAT | CAA | GAT | TAT | CAT | GGC | TTG | CCA | GAG | TTC | AGA | AAT | 492 |
|-----|-----|-----|-----|-----|-----|-----|-----|-----|-----|-----|-----|-----|-----|-----|
| Ala | Ile | Tyr | Gln | Asp | Tyr | His | Gly | Leu | Pro | Glu | Phe | Arg | Asn |     |
|     |  90 |     |     |     |     |  95 |     |     |     |     | 100 |     |     |     |

| GCT | GTA | GCA | AGG | TTC | ATG | GAG | AAG | GTG | AGA | GGT | GAC | AGA | GTC | 534 |
|-----|-----|-----|-----|-----|-----|-----|-----|-----|-----|-----|-----|-----|-----|-----|
| Ala | Val | Ala | Arg | Phe | Met | Glu | Lys | Val | Arg | Gly | Asp | Arg | Val |     |
|     |     | 105 |     |     |     |     | 110 |     |     |     |     | 115 |     |     |

| AAG | TTC | GAT | CCC | AAC | CGC | ATT | GTG | ATG | AGT | GGT | GGG | GCA | ACC | 576 |
|-----|-----|-----|-----|-----|-----|-----|-----|-----|-----|-----|-----|-----|-----|-----|
| Lys | Phe | Asp | Pro | Asn | Arg | Ile | Val | Met | Ser | Gly | Gly | Ala | Thr |     |
|     |     |     | 120 |     |     |     |     | 125 |     |     |     |     | 130 |     |

| GGA | GCT | CAT | GAA | ACT | CTG | GCC | TTC | TGT | TTA | GCT | GAC | CCT | GAA | 618 |
|-----|-----|-----|-----|-----|-----|-----|-----|-----|-----|-----|-----|-----|-----|-----|
| Gly | Ala | His | Glu | Thr | Leu | Ala | Phe | Cys | Leu | Ala | Asp | Pro | Glu |     |
|     |     |     |     | 135 |     |     |     |     | 140 |     |     |     |     |     |

| GAT | GCG | TTT | TTG | GTA | CCC | ACA | CCA | TAT | TAT | CCA | GGA | TTT | GAT | 660 |
|-----|-----|-----|-----|-----|-----|-----|-----|-----|-----|-----|-----|-----|-----|-----|
| Asp | Ala | Phe | Leu | Val | Pro | Thr | Pro | Tyr | Tyr | Pro | Gly | Phe | Asp |     |
| 145 |     |     |     |     | 150 |     |     |     |     | 155 |     |     |     |     |

| CGG | GAT | TTG | AGG | TGG | CGA | ACA | GGG | ATG | CAA | CTT | CTT | CCA | ATT | 702 |
|-----|-----|-----|-----|-----|-----|-----|-----|-----|-----|-----|-----|-----|-----|-----|
| Arg | Asp | Leu | Arg | Trp | Arg | Thr | Gly | Met | Gln | Leu | Leu | Pro | Ile |     |
|     | 160 |     |     |     |     | 165 |     |     |     |     | 170 |     |     |     |

| GTT | TGT | CGC | AGC | TCC | AAT | GAT | TTT | AAG | GTC | ACT | AAA | GAA | TCC | 744 |
|-----|-----|-----|-----|-----|-----|-----|-----|-----|-----|-----|-----|-----|-----|-----|
| Val | Cys | Arg | Ser | Ser | Asn | Asp | Phe | Lys | Val | Thr | Lys | Glu | Ser |     |

-continued

|  |  |  | 175 |  |  |  |  | 180 |  |  |  |  | 185 |  |  |
|---|---|---|---|---|---|---|---|---|---|---|---|---|---|---|---|
| ATG | GAA | GCT | GCT | TAT | CAG | AAA | GCT | CAA | GAA | GCC | AAC | ATC | AGA |  | 786 |
| Met | Glu | Ala | Ala | Tyr | Gln | Lys | Ala | Gln | Glu | Ala | Asn | Ile | Arg |  |  |
|  |  |  | 190 |  |  |  |  | 195 |  |  |  |  | 200 |  |  |

| GTA | AAG | GGG | TTC | CTC | TTA | AAT | AAT | CCA | TCA | AAT | CCA | TTG | GGA | 828 |
|---|---|---|---|---|---|---|---|---|---|---|---|---|---|---|
| Val | Lys | Gly | Phe | Leu | Leu | Asn | Asn | Pro | Ser | Asn | Pro | Leu | Gly |  |
|  |  |  |  | 205 |  |  |  |  | 210 |  |  |  |  |  |

| ACT | GTT | CTT | GAC | AGG | GAA | ACT | TTG | ATT | GAT | ATA | GTC | ACA | TTC | 870 |
|---|---|---|---|---|---|---|---|---|---|---|---|---|---|---|
| Thr | Val | Leu | Asp | Arg | Glu | Thr | Leu | Ile | Asp | Ile | Val | Thr | Phe |  |
| 215 |  |  |  |  | 220 |  |  |  |  | 225 |  |  |  |  |

| ATC | AAT | GAC | AAA | AAT | ATC | CAC | TTG | ATT | TGT | GAT | GAG | ATA | TAT | 912 |
|---|---|---|---|---|---|---|---|---|---|---|---|---|---|---|
| Ile | Asn | Asp | Lys | Asn | Ile | His | Leu | Ile | Cys | Asp | Glu | Ile | Tyr |  |
|  | 230 |  |  |  |  | 235 |  |  |  |  | 240 |  |  |  |

| TCT | GCC | ACC | GTC | TTC | AGC | CAG | CCC | GAA | TTC | ATC | AGC | ATC | TCT | 954 |
|---|---|---|---|---|---|---|---|---|---|---|---|---|---|---|
| Ser | Ala | Thr | Val | Phe | Ser | Gln | Pro | Glu | Phe | Ile | Ser | Ile | Ser |  |
|  |  | 245 |  |  |  |  | 250 |  |  |  |  | 255 |  |  |

| GAA | ATA | ATT | GAG | CAT | GAT | GTT | CAA | TGC | AAC | CGT | GAT | CTC | ATA | 996 |
|---|---|---|---|---|---|---|---|---|---|---|---|---|---|---|
| Glu | Ile | Ile | Glu | His | Asp | Val | Gln | Cys | Asn | Arg | Asp | Leu | Ile |  |
|  |  |  | 260 |  |  |  |  | 265 |  |  |  |  | 270 |  |

| CAT | CTT | GTG | TAT | AGC | CTG | TCC | AAG | GAC | TTG | GGC | TTC | CCT | GGA | 1038 |
|---|---|---|---|---|---|---|---|---|---|---|---|---|---|---|
| His | Leu | Val | Tyr | Ser | Leu | Ser | Lys | Asp | Leu | Gly | Phe | Pro | Gly |  |
|  |  |  |  | 275 |  |  |  |  | 280 |  |  |  |  |  |

| TTC | AGA | GTT | GGC | ATT | TTG | TAT | TCA | TAT | AAT | GAC | GCT | GTT | GTC | 1080 |
|---|---|---|---|---|---|---|---|---|---|---|---|---|---|---|
| Phe | Arg | Val | Gly | Ile | Leu | Tyr | Ser | Tyr | Asn | Asp | Ala | Val | Val |  |
| 285 |  |  |  |  | 290 |  |  |  |  | 295 |  |  |  |  |

| AGC | TGT | GCT | AGA | AAA | ATG | TCG | AGT | TTC | GGC | CTT | GTT | TCA | ACA | 1122 |
|---|---|---|---|---|---|---|---|---|---|---|---|---|---|---|
| Ser | Cys | Ala | Arg | Lys | Met | Ser | Ser | Phe | Gly | Leu | Val | Ser | Thr |  |
|  | 300 |  |  |  |  | 305 |  |  |  |  | 310 |  |  |  |

| CAA | ACT | CAG | CAT | CTG | ATT | GCA | TCA | ATG | TTA | TCG | GAC | GAA | GCA | 1164 |
|---|---|---|---|---|---|---|---|---|---|---|---|---|---|---|
| Gln | Thr | Gln | His | Leu | Ile | Ala | Ser | Met | Leu | Ser | Asp | Glu | Ala |  |
|  |  | 315 |  |  |  |  | 320 |  |  |  |  | 325 |  |  |

| TTT | ATG | GAC | AAA | ATC | ATT | TCC | ACG | AGC | TCA | GAG | AGA | TTA | GCT | 1206 |
|---|---|---|---|---|---|---|---|---|---|---|---|---|---|---|
| Phe | Met | Asp | Lys | Ile | Ile | Ser | Thr | Ser | Ser | Glu | Arg | Leu | Ala |  |
|  |  |  | 330 |  |  |  |  | 335 |  |  |  |  | 340 |  |

| GCA | AGG | CAT | GGT | CTT | TTC | ACA | AGA | GGA | CTT | GCT | CAA | GTA | GGC | 1248 |
|---|---|---|---|---|---|---|---|---|---|---|---|---|---|---|
| Ala | Arg | His | Gly | Leu | Phe | Thr | Arg | Gly | Leu | Ala | Gln | Val | Gly |  |
|  |  |  |  | 345 |  |  |  |  | 350 |  |  |  |  |  |

| ATT | GGC | ACC | TTA | AAA | AGC | AGT | GCG | GGC | CTT | TAT | TTC | TGG | ATG | 1290 |
|---|---|---|---|---|---|---|---|---|---|---|---|---|---|---|
| Ile | Gly | Thr | Leu | Lys | Ser | Ser | Ala | Gly | Leu | Tyr | Phe | Trp | Met |  |
| 355 |  |  |  |  | 360 |  |  |  |  | 365 |  |  |  |  |

| GAC | TTA | AGG | AGA | CTC | CTC | AGG | GAG | TCC | ACA | TTT | GAG | GCA | GAA | 1332 |
|---|---|---|---|---|---|---|---|---|---|---|---|---|---|---|
| Asp | Leu | Arg | Arg | Leu | Leu | Arg | Glu | Ser | Thr | Phe | Glu | Ala | Glu |  |
|  | 370 |  |  |  |  | 375 |  |  |  |  | 380 |  |  |  |

| ATG | GAA | CTT | TGG | AGG | ATC | ATA | ATA | CAT | GAA | GTC | AAG | CTC | AAT | 1374 |
|---|---|---|---|---|---|---|---|---|---|---|---|---|---|---|
| Met | Glu | Leu | Trp | Arg | Ile | Ile | Ile | His | Glu | Val | Lys | Leu | Asn |  |
|  |  | 385 |  |  |  |  | 390 |  |  |  |  | 395 |  |  |

| GTT | TCA | CCA | GGC | TTA | TCT | TTC | CAT | TGC | TCA | GAA | CCA | GGA | TGG | 1416 |
|---|---|---|---|---|---|---|---|---|---|---|---|---|---|---|
| Val | Ser | Pro | Gly | Leu | Ser | Phe | His | Cys | Ser | Glu | Pro | Gly | Trp |  |
|  |  |  | 400 |  |  |  |  | 405 |  |  |  |  | 410 |  |

| TTC | AGA | GTT | TGC | TTT | GCC | AAC | ATG | GAC | GAC | GAA | AGT | GTG | AGA | 1458 |
|---|---|---|---|---|---|---|---|---|---|---|---|---|---|---|
| Phe | Arg | Val | Cys | Phe | Ala | Asn | Met | Asp | Asp | Glu | Ser | Val | Arg |  |
|  |  |  |  | 415 |  |  |  |  | 420 |  |  |  |  |  |

| GTT | GCT | CTC | AGA | AGA | ATC | CAC | AAA | TTT | GTG | CTT | GTT | CAG | GGC | 1500 |
|---|---|---|---|---|---|---|---|---|---|---|---|---|---|---|
| Val | Ala | Leu | Arg | Arg | Ile | His | Lys | Phe | Val | Leu | Val | Gln | Gly |  |
| 425 |  |  |  |  | 430 |  |  |  |  | 435 |  |  |  |  |

| AAG | GCA | ACA | GAG | CCA | ACA | ACT | CCA | AAG | AGT | CGC | TGC | GGA | AGC | 1542 |
|---|---|---|---|---|---|---|---|---|---|---|---|---|---|---|
| Lys | Ala | Thr | Glu | Pro | Thr | Thr | Pro | Lys | Ser | Arg | Cys | Gly | Ser |  |
|  | 440 |  |  |  |  | 445 |  |  |  |  | 450 |  |  |  |

| AGC | AAA | CTT | CAA | CTC | AGC | TTA | TCT | TTC | CGC | AGA | TTG | GAC | GAA | 1584 |
|---|---|---|---|---|---|---|---|---|---|---|---|---|---|---|
| Ser | Lys | Leu | Gln | Leu | Ser | Leu | Ser | Phe | Arg | Arg | Leu | Asp | Glu |  |

|       |     |     |     |     |     |     |     |     |     |     |     |     |     |     |      |
|-------|-----|-----|-----|-----|-----|-----|-----|-----|-----|-----|-----|-----|-----|-----|------|
|       |     | 455 |     |     |     |     | 460 |     |     |     |     |     | 465 |     |      |
| AGG   | GTG | ATG | GGA | TCG | CAT | ATG | ATG | TCC | CCT | CAC | TCC | CCG | ATG |     | 1626 |
| Arg   | Val | Met | Gly | Ser | His | Met | Met | Ser | Pro | His | Ser | Pro | Met |     |      |
|       |     |     | 470 |     |     |     |     | 475 |     |     |     |     | 480 |     |      |
| GCT   | TCA | CCT | TTG | GTT | CGG | GCT | ACA | TAAATCATTT | CTTGATCAGA |  |  |  |  |  | 1670 |
| Ala   | Ser | Pro | Leu | Val | Arg | Ala | Thr |     |     |     |     |     |     |     |      |
|       |     |     |     | 485 |     |     |     |     |     |     |     |     |     |     |      |

```
TCATATAGCA AAGATTCCTG AGTAAATACT CGAAACCCTT TCTGGATAAC        1720

TGAAAAGAGA GTTGTTGATT CTTTGCTGTA TCATACAAAC ACGTTACAGG        1770

CATTTTTTGG CCATCTGATG CGTGCAAATT GCATCAAATG CTTTTATTAT        1820

TGTCATATTC ATTTGTGTAC CTTGGTTTTC CTTGCCCTTC AGTCCTCCTT        1870

GTTTTTTGTT TCTTTGTTAT TATTTCTTC CAGTTGATCA GTTAAACGAA         1920

GGAAGCTCAA TTGTTTCAAG CTATTAGTAA CAGATCATTT TGTAATAGCA        1970

ATAGTTTCAG GATTCTGAAA TGAAAGTTTA TCATTTTTCC ATCATTTTAA        2020

AAAAAAAAAA AAAAAAAAA                                          2040
```

( 2 ) INFORMATION FOR SEQ ID NO:12:

( i ) SEQUENCE CHARACTERISTICS:
        ( A ) LENGTH: 318 amino acid residues
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY:CDS
        ( B ) LOCATION:46..1003

( x i ) SEQUENCE DESCRIPTION: SEQ ID NO:12:

```
Met Ala Thr Phe Pro Leu Ile Asp Met Glu Lys Leu Asp Gly Glu
 1               5                  10                  15

Glu Arg Ala Ala Thr Met Gly Val Ile Lys Asp Ala Cys Glu Ser
                20                  25                  30

Trp Gly Phe Phe Glu Val Leu Asn His Gly Ile Ser Asn Glu Leu
                35                  40                  45

Met Asp Thr Val Glu Arg Leu Thr Lys Glu His Tyr Lys Lys Cys
                50                  55                  60

Met Glu Leu Lys Phe Lys Glu Met Val Glu Ser Lys Glu Leu Glu
                65                  70                  75

Ala Val Gln Thr Glu Ile Asn Asp Leu Asp Trp Glu Ser Thr Phe
                80                  85                  90

Phe Leu Arg His Leu Pro Val Ser Asn Ile Ser Glu Val Pro Asp
                95                 100                 105

Leu Asp Asp Glu Tyr Arg Lys Val Met Lys Glu Phe Ala Leu Gln
               110                 115                 120

Leu Glu Lys Leu Ala Glu Leu Leu Leu Asp Leu Leu Cys Glu Asn
               125                 130                 135

Leu Gly Leu Glu Lys Gly Tyr Leu Lys Lys Ala Phe Tyr Gly Thr
               140                 145                 150

Lys Gly Pro Thr Phe Gly Thr Lys Val Ser Asn Tyr Pro Pro Cys
               155                 160                 165

Pro Arg Pro Glu Leu Ile Lys Gly Leu Arg Ala His Thr Asp Ala
               170                 175                 180

Gly Gly Ile Ile Leu Leu Phe Gln Asp Asp Lys Val Ser Gly Leu
```

|     |     |     |     | 185 |     |     |     |     | 190 |     |     |     |     | 195 |
| --- | --- | --- | --- | --- | --- | --- | --- | --- | --- | --- | --- | --- | --- | --- |
| Gln | Leu | Leu | Lys | Asp | Gly | Glu | Trp | Val | Asp | Val | Pro | Pro | Met | Arg |
|     |     |     |     | 200 |     |     |     |     | 205 |     |     |     |     | 210 |
| His | Ser | Ile | Val | Ile | Asn | Ile | Gly | Asp | Gln | Leu | Glu | Val | Ile | Thr |
|     |     |     |     | 215 |     |     |     |     | 220 |     |     |     |     | 225 |
| Asn | Gly | Lys | Tyr | Lys | Ser | Val | Met | His | Arg | Val | Ile | Ala | Gln | Pro |
|     |     |     |     | 230 |     |     |     |     | 235 |     |     |     |     | 240 |
| Asp | Gly | Asn | Arg | Met | Ser | Leu | Ala | Ser | Phe | Tyr | Asn | Pro | Gly | Ser |
|     |     |     |     | 245 |     |     |     |     | 250 |     |     |     |     | 255 |
| Asp | Ala | Val | Ile | Tyr | Pro | Ala | Pro | Ala | Leu | Val | Glu | Lys | Glu | Ala |
|     |     |     |     | 260 |     |     |     |     | 265 |     |     |     |     | 270 |
| Glu | Asp | Lys | Gln | Ile | Tyr | Pro | Lys | Phe | Val | Phe | Glu | Asp | Tyr | Met |
|     |     |     |     | 275 |     |     |     |     | 280 |     |     |     |     | 285 |
| Lys | Leu | Tyr | Ala | Gly | Leu | Lys | Phe | Gln | Ala | Lys | Glu | Pro | Arg | Phe |
|     |     |     |     | 290 |     |     |     |     | 295 |     |     |     |     | 300 |
| Glu | Ala | Met | Lys | Ala | Val | Glu | Ser | Thr | Val | Asn | Leu | Gly | Pro | Ile |
|     |     |     |     | 305 |     |     |     |     | 310 |     |     |     |     | 315 |
| Ala | Thr | Val |     |     |     |     |     |     |     |     |     |     |     |     |
|     |     | 318 |     |     |     |     |     |     |     |     |     |     |     |     |

(2) INFORMATION FOR SEQ ID NO:13:

(i) SEQUENCE CHARACTERISTICS:
        (A) LENGTH: 1320 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: CDS
        (B) LOCATION: 46..1003

(xi) SEQUENCE DESCRIPTION: SEQ ID NO:13:

```
TGTAAACGAA  GCATAAGCAC  AAGCAAACAC  AAACTAGAAA  GAGAG ATG                        48
                                                      Met
                                                       1

GCT  ACA  TTC  CCC  CTA  ATC  GAC  ATG  GAG  AAG  CTT  GAC  GGT  GAA             90
Ala  Thr  Phe  Pro  Leu  Ile  Asp  Met  Glu  Lys  Leu  Asp  Gly  Glu
               5                   10                         15

GAG  AGG  GCT  GCC  ACT  ATG  GGA  GTC  ATA  AAA  GAT  GCT  TGT  GAA            132
Glu  Arg  Ala  Ala  Thr  Met  Gly  Val  Ile  Lys  Asp  Ala  Cys  Glu
                    20                   25

AGC  TGG  GGC  TTC  TTT  GAG  GTG  TTG  AAT  CAT  GGG  ATA  TCT  AAT            174
Ser  Trp  Gly  Phe  Phe  Glu  Val  Leu  Asn  His  Gly  Ile  Ser  Asn
30                        35                        40

GAG  CTC  ATG  GAC  ACA  GTG  GAG  AGG  CTA  ACA  AAG  GAG  CAT  TAC            216
Glu  Leu  Met  Asp  Thr  Val  Glu  Arg  Leu  Thr  Lys  Glu  His  Tyr
     45                        50                        55

AAG  AAA  TGT  ATG  GAA  CTA  AAG  TTC  AAG  GAA  ATG  GTG  GAG  AGC            258
Lys  Lys  Cys  Met  Glu  Leu  Lys  Phe  Lys  Glu  Met  Val  Glu  Ser
               60                   65                        70

AAG  GAA  TTG  GAA  GCT  GTT  CAG  ACT  GAG  ATC  AAT  GAT  TTG  GAC            300
Lys  Glu  Leu  Glu  Ala  Val  Gln  Thr  Glu  Ile  Asn  Asp  Leu  Asp
                    75                   80                        85

TGG  GAA  AGT  ACC  TTC  TTC  TTG  CGC  CAT  CTT  CCT  GTT  TCC  AAC            342
Trp  Glu  Ser  Thr  Phe  Phe  Leu  Arg  His  Leu  Pro  Val  Ser  Asn
                    90                        95

ATC  TCA  GAA  GTC  CCT  GAT  CTT  GAT  GAT  GAA  TAC  AGA  AAG  GTT            384
Ile  Ser  Glu  Val  Pro  Asp  Leu  Asp  Asp  Glu  Tyr  Arg  Lys  Val
```

```
                                                              -continued
100                     105                           110

ATG AAG GAA TTT GCG TTG CAA CTT GAG AAA CTA GCA GAG CTC         426
Met Lys Glu Phe Ala Leu Gln Leu Glu Lys Leu Ala Glu Leu
    115                 120                 125

CTG TTG GAC TTG CTA TGC GAG AAC CTT GGC CTA GAG AAA GGC         468
Leu Leu Asp Leu Leu Cys Glu Asn Leu Gly Leu Glu Lys Gly
        130                 135                 140

TAT CTG AAG AAA GCC TTC TAT GGC ACC AAA GGA CCA ACC TTT         510
Tyr Leu Lys Lys Ala Phe Tyr Gly Thr Lys Gly Pro Thr Phe
            145                 150                 155

GGC ACC AAA GTC AGC AAT TAC CCT CCA TGC CCT CGT CCA GAA         552
Gly Thr Lys Val Ser Asn Tyr Pro Pro Cys Pro Arg Pro Glu
                160                 165

CTG ATC AAG GGC CTC CGG GCA CAC ACC GAT GCC GGC GGC ATC         594
Leu Ile Lys Gly Leu Arg Ala His Thr Asp Ala Gly Gly Ile
170                 175                 180

ATC CTG CTG TTC CAG GAT GAC AAG GTC AGC GGT CTC CAG CTC         636
Ile Leu Leu Phe Gln Asp Asp Lys Val Ser Gly Leu Gln Leu
    185                 190                 195

CTC AAG GAT GGT GAA TGG GTG GAT GTT CCG CCT ATG CGC CAC         678
Leu Lys Asp Gly Glu Trp Val Asp Val Pro Pro Met Arg His
        200                 205                 210

TCC ATT GTA ATC AAC ATC GGC GAC CAA CTT GAG GTA ATC ACA         720
Ser Ile Val Ile Asn Ile Gly Asp Gln Leu Glu Val Ile Thr
            215                 220                 225

AAT GGA AAA TAC AAG AGT GTG ATG CAC CGG GTG ATA GCT CAA         762
Asn Gly Lys Tyr Lys Ser Val Met His Arg Val Ile Ala Gln
                230                 235

CCA GAT GGG AAC AGA ATG TCA CTA GCA TCA TTC TAC AAT CCA         804
Pro Asp Gly Asn Arg Met Ser Leu Ala Ser Phe Tyr Asn Pro
240                 245                 250

GGA AGT GAT GCA GTG ATC TAT CCA GCA CCG GCA TTG GTT GAG         846
Gly Ser Asp Ala Val Ile Tyr Pro Ala Pro Ala Leu Val Glu
    255                 260                 265

AAA GAG GCA GAG GAC AAG CAG ATA TAT CCC AAG TTT GTG TTC         888
Lys Glu Ala Glu Asp Lys Gln Ile Tyr Pro Lys Phe Val Phe
        270                 275                 280

GAG GAC TAC ATG AAG CTC TAT GCT GGC CTT AAG TTC CAA GCT         930
Glu Asp Tyr Met Lys Leu Tyr Ala Gly Leu Lys Phe Gln Ala
            285                 290                 295

AAA GAG CCC AGG TTT GAA GCC ATG AAG GCC GTG GAA AGC ACC         972
Lys Glu Pro Arg Phe Glu Ala Met Lys Ala Val Glu Ser Thr
                300                 305

GTA AAC TTG GGT CCA ATC GCA ACT GTT TGAGATAATA CACGCTTTGA      1019
Val Asn Leu Gly Pro Ile Ala Thr Val
310                 315

TCTGCTGCTG TCTTATAATG CGCGTTTGCG TAATCATATC CTAGCATAGT         1069

ATATCTGAGA TCTGAGTCTG TATTGTGGTG TGAGTTTGGT TTAGCCCCTT         1119

GTTAATGCTT GGATTGGACT AGTTAAATGT GGAGCTGGTT TGTTAGATAA         1169

GATAGTCTTG CCAGGATCTT TGAGTAAATA TGATTCTGCG GAAGTCTGCG         1219

GTGAATGATA ACGTGTAAAG CAATCCGAAA GTTACCTTTC TGGGGCTTTG         1269

TCATATGCAA TGGAGAAGGA ATCTTCCAAA AAAAAAAAAA AAAAAAAA          1319

A                                                              1320
```

We claim:

1. A substantially pure ACC synthase from *Coffea arabica* comprising the amino acid sequence: (SEQ ID NO:10).

2. A substantially pure nucleic acid comprising the nucleotide sequence set forth in SEQ ID NO:11.

3. A substantially pure nucleic acid sequence that codes on expression for the amino acid sequence: (SEQ ID NO:10).

4. A substantially pure ACC oxidase from *Coffea arabica* comprising the amino acid sequence: (SEQ ID NO:12).

5. A substantially pure nucleic acid comprising the nucleotide sequence set forth in SEQ ID NO:13.

6. A substantially pure nucleic acid sequence that codes on expression for the amino acid sequence: (SEQ ID NO:12).

7. A transforming vector comprising a transcription promoter operably linked to:
   (a) the nucleic acid sequence: SEQ ID NO:11; or
   (b) a nucleic acid sequence that codes on expression for the amino acid sequence: SEQ ID NO:10; or
   (c) the nucleic acid sequence: SEQ ID NO:13; or
   (d) a nucleic acid sequence that codes on expression for the amino acid sequence: SEQ ID NO:12.

8. The transforming vector of claim 7, wherein the nucleic acid sequence is operably linked to the transcription promoter in a sense orientation.

9. The transforming vector of claim 7, wherein the nucleic acid sequence is operably linked to the transcription promoter in an antisense orientation.

10. A coffee plant transformed with a nucleic acid sequence that codes on transcription for an RNA that is antisense to the mRNA that codes on expression for an ACC synthase having the amino acid sequence: SEQ ID NO:10, wherein the RNA has a length sufficient to interfere with the expression of the ACC synthase.

11. A coffee bean from the coffee plant of claim 10.

12. A coffee plant transformed with a nucleic acid sequence that codes on transcription for an RNA that is antisense to the mRNA that codes on expression for an ACC oxidase having the amino acid sequence: SEQ ID NO:12, wherein the RNA has a length sufficient to interfere with the expression of the ACC oxidase.

13. A coffee bean from the coffee plant of claim 12.

14. A coffee plant transformed with (i) a first nucleic acid sequence that codes on transcription for a first RNA that is antisense to the mRNA that codes on expression for an ACC synthase having the amino acid sequence: SEQ ID NO.10, wherein the first RNA has a length sufficient to interfere with the expression of the ACC synthase, and (ii) a second nucleic acid sequence that codes on transcription for a second RNA that is antisense to the mRNA that codes on expression for an ACC oxidase having the amino acid sequence: SEQ ID NO:12, wherein the second RNA has a length sufficient to interfere with the expression of the ACC oxidase.

15. A coffee bean from the coffee plant of claim 14.

16. A coffee plant transformed with a nucleic acid sequence that codes on expression for the amino acid sequence: (SEQ ID NO:10).

17. The coffee plant of claim 16, wherein the nucleic acid sequence is linked to a transcription promoter in an antisense orientation.

18. The coffee plant of claim 16, wherein the nucleic acid sequence is linked to a transcription promoter in a sense orientation.

19. A coffee plant transformed with a nucleic acid sequence that codes on expression for the amino acid sequence: (SEQ ID NO:12).

20. A coffee plant transformed with a first nucleic acid sequence that codes on expression for the amino acid sequence: (SEQ ID No:10), and a second nucleic acid comprising the nucleotide sequence that codes on expression for the amino acid sequence (SEQ ID NO: 12).

21. A transformed coffee plant produced by the process of inserting into the plant genome a nucleic acid sequence that codes on transcription for an RNA that is antisense to the mRNA that codes on expression for an ACC synthase having the amino acid seguence: SEQ ID NO:10.

22. A transformed coffee plant produced by the process of inserting into the plant genome a nucleic acid sequence that codes on transcription for an RNA that is antisense to the mRNA that codes on expression for an ACC oxidase having the amino acid sequence: SEQ ID NO:12.

23. A transformed coffee plant produced by the process of inserting into the plant genome (i) a nucleic acid sequence that codes on transcription for an RNA that is antisense to the mRNA that codes on expression for an ACC synthase having the amino acid sequence: SEQ ID NO:10, and (ii) a nucleic acid sequence that codes on transcription for an RNA that is antisense to the mRNA that codes on expression for an ACC oxidase having the amino acid sequence: SEQ ID NO:12.

24. A coffee plant cell transformed with a nucleic acid sequence that codes on expression for the amino acid, sequence: (SEQ ID NO:10).

25. The coffee plant cell of claim 24, wherein the nucleic acid sequence is operably linked to a transcription promoter in an antisense orientation.

26. A coffee plant cell transformed with a nucleic acid sequence that codes on expression for the amino acid sequence: (SEQ ID NO:12).

27. The coffee plant cell of claim 26, wherein the nucleic acid sequence is operably linked to a transcription promoter in an antisense orientation.

28. A coffee plant cell transformed with (i) a nucleic acid sequence that codes on expression for the amino acid sequence: (SEQ ID NO:10), and (ii) a nucleic acid sequence that codes on expression for the amino acid sequence: (SEQ ID NO:12).

29. The coffee plant cell of claim 28, wherein at least one of said nucleic acid sequences is operably linked to a transcription promoter in an antisense orientation.

30. A method for transforming a coffee plant cell with a nucleic acid sequence that codes on transcription for an RNA that is antisense to the mRNA that codes for an ACC synthase from a coffee plant, comprising the steps of:
   providing a transforming vector comprising a nucleic acid sequence that codes on transcription for an RNA that has a length sufficient to interfere with the expression of an ACC synthase having the amino acid sequence: SEQ ID NO:10, wherein the nucleic acid sequence is operably linked to a transcription promoter in an antisense orientation; and
   inserting the transforming vector into a coffee plant cell, wherein the nucleic acid sequence thereafter becomes inserted into the genome of the coffee plant cell.

31. A method for transforming a coffee plant cell with a nucleic acid sequence that codes on transcription for an RNA that is antisense to the mRNA that codes for an ACC oxidase from a coffee plant, comprising the steps of:

provided a transforming vector comprising a nucleic acid sequence that codes on transcription for an RNA that has a length sufficient to interfere with the expression of an ACC oxidase having the amino acid sequence: SEQ ID NO:12, wherein the nucleic acid sequence is operably linked to a transcription promoter in an antisense orientation; and inserting the transforming vector into a coffee plant cell, wherein the nucleic acid sequence thereafter becomes inserted into the genome of the coffee plant cell.

32. A method for transforming a coffee plant cell with (i) a nucleic acid sequence that codes on transcription for an RNA that is antisense to the mRNA that codes for an ACC synthase from a coffee plant, and (ii) a nucleic acid sequence that codes on transcription for an RNA that is antisense to the mRNA that codes for an ACC oxidase from a coffee plant, comprising the steps of:

providing a first transforming vector comprising a first nucleic acid sequence that codes on transcrption for an RNA that has a length sufficient to interfere with the expression of an ACC synthase having the amino acid sequence: SEQ ID NO:10, wherein said first nucleic acid sequence is operably linked to a transcription promoter in an antisense orientation;

providing a second transforming vector comprising a second nucleic acid sequence that codes on transcription for an RNA that has a length sufficient to interfere with the expression an ACC oxidase having the amino acid sequence: SEQ ID NO:12, wherein the second nucleic acid sequence is operably linked to a transcription promoter in an antisense orientation; and inserting said transforming vectors into a coffee plant cell, wherein each of said nucleic acid sequences thereafter becomes inserted into the genome of the coffee plant cell.

33. A method for transforming a coffee plant cell with a nucleic acid sequence that codes on transcription for an RNA that is sense in orientation to the mRNA that codes for an ACC synthase from a coffee plant, comprising the steps of:

providing a transforming vector comprising a nucleic acid sequence that codes on transcription for an RNA that has a length sufficient to interfere with the expression of an ACC synthase having the amino acid sequence: SEQ ID NO:10, wherein the nucleic acid sequence is operably linked to a promoter in a sense orientation; and inserting the transforming vector into a coffee plant cell, wherein the nucleic acid sequence thereafter become inserted into the genome of the coffee plant cell.

34. A method for transforming a coffee plant cell with a nucleic acid sequence that codes on transcription for an RNA that is sense in orientation to the mRNA that codes for an ACC oxidase from a coffee plant, comprising the steps of:

providing a transforming vector comprising a nucleic acid sequence that codes on for an RNA that has a length sufficient to interfere with the expression of an ACC oxidase having the amino acid sequence: SEQ ID NO:12, wherein the nucleic acid sequence is operably linked to a transcription promoter in a sense orientation; and inserting the transforming vector into a coffee plant cell, wherein the nucleic acid sequence thereafter become inserted into the genome of the coffee plant cell.

35. A method for transforming a coffee plant cell with (i) a nucleic acid sequence that codes on transcription for an RNA that is sense in orientation to the mRNA that codes for an ACC synthase from a coffee plant, and (ii) a nucleic acid sequence that codes on transcription for an RNA that is sense in orientation to the mRNA that codes for an ACC oxidase from a coffee plant, comprising the steps of:

providing a first transforming vector comprising a first nucleic acid sequence that codes on transcription for an RNA that has a length sufficient to interfere with the expression of an ACC synthase having the amino acid sequence: SEQ ID NO:10, wherein said first nucleic acid sequence is operably linked to a transcription promoter in a sense orientation;

providing a second transforming vector comprising a second nucleic acid sequence that codes on transcription for an RNA that has a length sufficient to interfere with the expression of an ACC oxidase having the amino acid sequence: SEQ ID NO:12, wherein the second nucleic acid sequence is operably linked to a transcription promoter in a sense orientation; and inserting said transforming vectors into a coffee plant cell, wherein each of said nucleic acid sequences thereafter becomes inserted into the genome of the coffee plant cell.

36. A transformed coffee plant cell produced by the process of inserting a transforming vector into a coffee plant cell, wherein the transforming vector comprises a transcription promoter operably linked to (i) a nucleic acid sequence that codes on expression for the amino acid sequence: SEQ ID No:10, or (ii) a nucleic acid sequence that codes on expression for the amino acid sequence: SEQ ID NO:12.

37. The transformed coffee plant cell of claim 36, wherein the nucleic acid sequence is operably linked to the transcription promoter in a sense orientation.

38. A coffee plant regenerated from the transformed coffee plant cell of claim 37.

39. The transformed coffee plant cell of claim 36, wherein the nucleic acid sequence is operably linked to the transcription promoter in an antisense orientation.

40. A coffee plant regenerated from the transformed coffee plant cell of claim 39.

41. A coffee plant regenerated from the transformed coffee plant cell of claim 36.

42. A transformed coffee plant cell produced by the process of inserting a first transforming vector and a second transforming vector into a coffee plant cell, wherein the first transforming vector comprises a transcription promoter operably linked to a nucleic acid sequence that codes on expression for the amino acid sequence: SEQ ID NO:10, and the second transforming vector comprises a transcription promoter operably linked to a nucleic acid sequence that codes on expression for the amino acid sequence SEQ ID NO:12.

43. The transformed coffee plant cell of claim 42, wherein at least one of the nucleic acid sequences is operably linked to its transcription promoter in an antisense orientation.

44. A coffee plant regenerated from the transformed coffee plant cell of claim 42.

45. A coffee plant regenerated from the transformed coffee plant cell of claim 43.

46. A transformed coffee plant produced by the process of inserting into the plant genome a nucleic acid sequence that codes on transcription for an RNA that is sense to the mRNA that codes on expression for an ACC synthase having the amino acid sequence: SEQ ID NO:10.

47. A transformed coffee plant produced by the process of inserting into the plant genome a nucleic acid sequence that codes on transcription for an RNA that is sense to the mRNA that codes on expression for an ACC oxidase having the amino acid sequence: SEQ ID NO:12.

48. A transformed coffee plant produced by the process of inserting into the plant genome (i) a nucleic acid sequence that codes on transcription for an RNA that is sense to the mRNA that codes on expression for an ACC synthase having the amino acid sequence: SEQ ID NO:10, and (ii) a nucleic acid sequence that codes on transcription for an RNA that is sense to the mRNA that codes on expression for an ACC oxidase having the amino acid sequence: SEQ ID NO:12.

* * * * *

UNITED STATES PATENT AND TRADEMARK OFFICE
CERTIFICATE OF CORRECTION

PATENT NO. : 5,874,269
DATED : Feb. 23, 1999
INVENTOR(S) : John I. Stiles; Istefo Moisyadi; Kabi Raj Neupane It is certified that error appears in the above-indentified patent and that said Letters Patent is hereby corrected as shown below:

```
Column 37 should read Column 31
Column 38 should read Column 32
Column 39 should read Column 33
Column 40 should read Column 34
Column 41 should read Column 35
Column 42 should read Column 36
```

Signed and Sealed this

Twenty-fourth Day of August, 1999

Attest:

Q. TODD DICKINSON

*Attesting Officer*      *Acting Commissioner of Patents and Trademarks*

UNITED STATES PATENT AND TRADEMARK OFFICE
CERTIFICATE OF CORRECTION

PATENT NO. : 5,874,269  
DATED : February 23, 1999  
INVENTOR(S) : John I. Stiles, et al Page 1 of 7

It is certified that error appears in the above-identified patent and that said Letters Patent is hereby corrected as shown below:

After "SEQUENCE LISTING (1) GENERAL INFORMATION:

(III) NUMBER OF SEQUENCES: 13",

Please delete "(2) INFORMATION FOR SEQ ID NO:1: ....(2) INFORMATION FOR SEQ ID NO:9:...AAWTAWCAHG GNACWTATTG  20", and insert --(2) INFORMATION FOR SEQ ID NO:1:

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: other nucleic acid
    A) DESCRIPTION: primer (v) FRAGMENT TYPE: Internal fragment (xi) SEQUENCE DESCRIPTION: SEQ ID NO:1:

GAGAGAGAGA GAGAGAGAGA ACTAGTCTCG AGTTTTTTTT TTTTTTTTTT   50

(2) INFORMATION FOR SEQ ID NO:2:

UNITED STATES PATENT AND TRADEMARK OFFICE
CERTIFICATE OF CORRECTION

PATENT NO. : 5,874,269  
DATED : February 23, 1999  
INVENTOR(S) : John I. Stiles, et al Page 2 of 7

It is certified that error appears in the above-identified patent and that said Letters Patent is hereby corrected as shown below:

(i)   SEQUENCE CHARACTERISTICS:
        (A) LENGTH: 13 base pairs
        (B) TYPE: nucleic acid
        (D) TOPOLOGY: linear (ii)  MOLECULE TYPE: other nucleic acid
        (A)   DESCRIPTION: primer (v)   FRAGMENT TYPE: Internal fragment (xi)  SEQUENCE DESCRIPTION: SEQ ID NO:2:

AATTCGGCAC GAG            13

(2)   INFORMATION FOR SEQ ID NO:3:

(i)   SEQUENCE CHARACTERISTICS:
        (A)   LENGTH: 15 base pairs
        (B)   TYPE: nucleic acid
        (C)   STRANDEDNESS: single
        (D)   TOPOLOGY: linear (ii)  MOLECULE TYPE: OTHER NUCLEIC ACID
        (A)   DESCRIPTION: PRIMER (v)   FRAGMENT TYPE: Internal (xi)  SEQUENCE DESCRIPTION: SEQ ID NO:3:

UNITED STATES PATENT AND TRADEMARK OFFICE
CERTIFICATE OF CORRECTION

PATENT NO. : 5,874,269  Page 3 of 7
DATED : February 23, 1999
INVENTOR(S) : John I. Stiles, et al It is certified that error appears in the above-identified patent and that said Letters Patent is hereby corrected as shown below:

```
            GCCAAGCTTC CRTGRTARTC YTGRAA          15

(2)  INFORMATION FOR SEQ ID NO:4:

(i)   SEQUENCE CHARACTERISTICS:
              (A)  LENGTH: 10 base pairs
              (B)  TYPE:  nucleic acid
              (C)  STRANDEDNESS:  single
              (D)  TOPOLOGY:  linear (ii)  MOLECULE TYPE: OTHER NUCLEAR ACID
              (A)  DESCRIPTION:    PRIMER (v)   FRAGMENT TYPE: INTERNAL (xi)  SEQUENCE DESCRIPTION: SEQ ID NO:4:

TTYCARGAYT AYCAYGGHYT              10

(2)  INFORMATION FOR SEQ ID NO:5:

(i)   SEQUENCE CHARACTERISTICS:
              (A)  LENGTH:  10 base pairs
              (B)  TYPE:  nucleic acid
              (C)  STRANDEDNESS:  single
              (D)  TOPOLOGY:  linear
```

UNITED STATES PATENT AND TRADEMARK OFFICE
CERTIFICATE OF CORRECTION

PATENT NO. : 5,874,269
DATED : February 23, 1999
INVENTOR(S) : John I. Stiles, et al Page 4 of 7

It is certified that error appears in the above-identified patent and that said Letters Patent is hereby corrected as shown below:

```
        (ii) MOLECULE TYPE: OTHER NUCLEIC ACID
             (A)   DESCRIPTION:   PRIMER (v)  FRAGMENT TYPE: INTERNAL (xi) SEQUENCE DESCRIPTION: SEQ ID NO:5:

CCHGGDARNC CYAWRTCTTT              10

(2)  INFORMATION FOR SEQ ID NO:6:

(i)  SEQUENCE CHARACTERISTICS:
             (A)   LENGTH:   10 base pairs
             (B)   TYPE:   nucleic acid
             (C)   STRANDEDNESS:   single
             (D)   TOPOLOGY:   linear (ii) MOLECULE TYPE:   OTHER NUCLEIC ACID
             (A)   DESCRIPTION:   PRIMER (v)  FRAGMENT TYPE: INTERNAL (xi) SEQUENCE DESCRIPTION: SEQ ID NO:6:

TAATACGACT CACTATAGGG              10
```

UNITED STATES PATENT AND TRADEMARK OFFICE
CERTIFICATE OF CORRECTION

PATENT NO. : 5,874,269
DATED : February 23, 1999
INVENTOR(S) : John I. Stiles, et al It is certified that error appears in the above-identified patent and that said Letters Patent is hereby corrected as shown below:

```
   (2)   INFORMATION FOR SEQ ID NO:7:

(i)   SEQUENCE CHARACTERISTICS:
               (A)  LENGTH:   10 base pairs
               (B)  TYPE:  nucleic acid
               (C)  STRANDEDNESS:  single
               (D)  TOPOLOGY:  linear (ii) MOLECULE TYPE:  OTHER NUCLEIC ACID
               (A)  DESCRIPTION:  PRIMER (v)  FRAGMENT TYPE:  INTERNAL (xi) SEQUENCE DESCRIPTION: SEQ ID NO:7:

AATTAACCCT CACTAAAGGG              10

(2)   INFORMATION FOR SEQ ID NO:8:

(i)   SEQUENCE CHARACTERISTICS:
               (A)  LENGTH: 9 base pairs
               (B)  TYPE: nucleic acid
               (C)  STRANDEDNESS: single
               (D)  TOPOLOGY: linear (ii) MOLECULE TYPE: OTHER NUCLEIC ACID
               (A)  DESCRIPTION:  PRIMER
```

UNITED STATES PATENT AND TRADEMARK OFFICE
CERTIFICATE OF CORRECTION

PATENT NO. : 5,874,269
DATED : February 23, 1999
INVENTOR(S) : John I. Stiles, et al It is certified that error appears in the above-identified patent and that said Letters Patent is hereby corrected as shown below:

(v)  FRAGMENT TYPE: Internal (xi) SEQUENCE DESCRIPTION: SEQ ID NO:8:

TCATIGCKKC RAKIGGTTC        9

(2)  INFORMATION FOR SEQ ID NO:9:

(i)  SEQUENCE CHARACTERISTICS:
        (A)  LENGTH:  00 base pairs
        (B)  TYPE:  nucleic acid
        (C)  STRANDEDNESS:  single
        (D)  TOPOLOGY:  linear (ii) MOLECULE TYPE: OTHER NUCLEIC ACID
        (A)  DESCRIPTION:  PRIMER (v)  FRAGMENT TYPE:  Internal

UNITED STATES PATENT AND TRADEMARK OFFICE
CERTIFICATE OF CORRECTION

PATENT NO. : 5,874,269
DATED : February 23, 1999
INVENTOR(S) : John I. Stiles, et al It is certified that error appears in the above-identified patent and that said Letters Patent is hereby corrected as shown below:

```
(xi) SEQUENCE DESCRIPTION: SEQ ID NO:9:

GACACTGTGG AGAGGCTGAC            10 --.
```

Signed and Sealed this

Fifteenth Day of May, 2001

Attest:

NICHOLAS P. GODICI

Attesting Officer    Acting Director of the United States Patent and Trademark Office

UNITED STATES PATENT AND TRADEMARK OFFICE
CERTIFICATE OF CORRECTION

PATENT NO.    : 5,874,269
DATED         : February 23, 1999
INVENTOR(S)   : John I. Stiles, Istefo Moisyadi & Kabi Raj Neupane It is certified that error appears in the above-identified patent and that said Letters Patent is hereby corrected as shown below:

After "SEQUENCE LISTING (1) GENERAL INFORMATION:
    (III)  NUMBER OF SEQUENCES: 13", Please delete " (2) INFORMATION FOR SEQ ID NO:1:
.... (2) INFORMATION FOR SEQ ID NO:9:...AAWTAWCAHG GNACWTATTG  20", and insert -- (2) INFORMATION FOR SEQ ID NO:1:

(i)   SEQUENCE CHARACTERISTICS:
        (A)  LENGTH: 50 base pairs
        (B)  TYPE: nucleic acid
        (C)  STRANDEDNESS: single
        (D)  TOPOLOGY: linear (ii)  MOLECULE TYPE: other nucleic acid
        (A)  DESCRIPTION: primer (v)   FRAGMENT TYPE: Internal fragment (xi)  SEQUENCE DESCRIPTION: SEQ ID NO:1:

GAGAGAGAGA GAGAGAGAGA ACTAGTCTCG AGTTTTTTTT
    TTTTTTTTTT                                         50

(2) INFORMATION FOR SEQ ID NO:2:

(i)   SEQUENCE CHARACTERISTICS:
        (A)  LENGTH: 13 base pairs
        (B)  TYPE: nucleic acid
        (D)  TOPOLOGY: linear (ii)  MOLECULE TYPE: other nucleic acid
        (A)  DESCRIPTION: primer

UNITED STATES PATENT AND TRADEMARK OFFICE
CERTIFICATE OF CORRECTION

PATENT NO. : 5,874,269
DATED : February 23, 1999
INVENTOR(S) : John I. Stiles, Istefo Moisyadi & Kabi Raj Neupane It is certified that error appears in the above-identified patent and that said Letters Patent is hereby corrected as shown below:

(v)    FRAGMENT TYPE: Internal fragment (xi)    SEQUENCE DESCRIPTION: SEQ ID NO:2:

AATTCGCAC GAG        13

(2) INFORMATION FOR SEQ ID NO:3:

(i)    SEQUENCE CHARACTERISTICS:
        (A)    LENGTH: 26 base pairs
        (B)    TYPE: nucleic acid
        (C)    STRANDEDNESS: single
        (D)    TOPOLOGY: linear (ii)    MOLECULE TYPE: OTHER NUCLEIC ACID
        (A)    DESCRIPTION: PRIMER (v)    FRAGMENT TYPE : Internal (ix)    FEATURE
        (D)    OTHER INFORMATION:
        R is G or A
        Y is T/U or C (xi)    SEQUENCE DESCRIPTION: SEQ ID NO:3:

GCCAAGCTTC CRTGRTARTC YTGRAA        26

(2)    INFORMATION FOR SEQ ID NO:4:

(i)    SEQUENCE CHARACTERISTICS:
        (A)    LENGTH: 20 base pairs
        (B)    TYPE: nucleic acid
        (C)    STRANDEDNESS: single
        (D)    TOPOLOGY: linear

UNITED STATES PATENT AND TRADEMARK OFFICE
CERTIFICATE OF CORRECTION

PATENT NO.   : 5,874,269
DATED        : February 23, 1999
INVENTOR(S)  : John I. Stiles, Istefo Moisyadi & Kabi Raj Neupane It is certified that error appears in the above-identified patent and that said Letters Patent is hereby corrected as shown below:

(ii)    MOLECULE TYPE: OTHER NUCLEAR ACID
           (A)    DESCRIPTION: PRIMER (v)    FRAGMENT TYPE : INTERNAL (ix)    FEATURE
           (D)    OTHER INFORMATION:
                R is G or A
                Y is T/U or C
                H is A or C or T/U (xi)    SEQUENCE DESCRIPTION: SEQ ID NO:4:

TTYCARGAYT AYCAYGGHYT                             20

(2) INFORMATION FOR SEQ ID NO:5:

(i)    SEQUENCE CHARACTERISTICS:
           (A)    LENGTH: 20 base pairs
           (B)    TYPE: nucleic acid
           (C)    STRANDEDNESS: single
           (D)    TOPOLOGY: linear (ii)    MOLECULE TYPE: OTHER NUCLEIC ACID
           (A)    DESCRIPTION: PRIMER (v)    FRAGMENT TYPE : INTERNAL (ix)    FEATURE
           (D)    OTHER INFORMATION:
                H is A or C or T/U
                D is A or G or T/U
                R is G or A
                W is A or T/U
                Y is T/U or C
                N is A or C or G or T/U

UNITED STATES PATENT AND TRADEMARK OFFICE
CERTIFICATE OF CORRECTION

PATENT NO.   : 5,874,269
DATED         : February 23, 1999
INVENTOR(S) : John I. Stiles, Istefo Moisyadi & Kabi Raj Neupane It is certified that error appears in the above-identified patent and that said Letters Patent is hereby corrected as shown below:

(xi)    SEQUENCE DESCRIPTION: SEQ ID NO:5:

CCHGGDARNC CYAWRTCTTT              20

(2) INFORMATION FOR SEQ ID NO:6:

(i)    SEQUENCE CHARACTERISTICS:
            (A)    LENGTH: 20 base pairs
            (B)    TYPE: nucleic acid
            (C)    STRANDEDNESS: single
            (D)    TOPOLOGY: linear (ii)    MOLECULE TYPE: OTHER NUCLEIC ACID
            (A)    DESCRIPTION: PRIMER (v)    FRAGMENT TYPE : INTERNAL (xi)    SEQUENCE DESCRIPTION: SEQ ID NO:6:

TAATACGACT CACTATAGGG              20

(2) INFORMATION FOR SEQ ID NO:7:

(i)    SEQUENCE CHARACTERISTICS:
            (A)    LENGTH: 20 base pairs
            (B)    TYPE: nucleic acid
            (C)    STRANDEDNESS: single
            (D)    TOPOLOGY: linear (ii)    MOLECULE TYPE: OTHER NUCLEIC ACID
            (A)    DESCRIPTION: PRIMER (v)    FRAGMENT TYPE : INTERNAL

UNITED STATES PATENT AND TRADEMARK OFFICE
CERTIFICATE OF CORRECTION

PATENT NO.  : 5,874,269  
DATED       : February 23, 1999  
INVENTOR(S) : John I. Stiles, Istefo Moisyadi & Kabi Raj Neupane It is certified that error appears in the above-identified patent and that said Letters Patent is hereby corrected as shown below:

(xi)    SEQUENCE DESCRIPTION: SEQ ID NO:7:

AATTAACCCT CACTAAAGGG          20

(2) INFORMATION FOR SEQ ID NO:8:

(i)    SEQUENCE CHARACTERISTICS:
- (A) LENGTH: 19 base pairs
- (B) TYPE: nucleic acid
- (C) STRANDEDNESS: single
- (D) TOPOLOGY: linear (ii)    MOLECULE TYPE: OTHER NUCLEIC ACID
- (A) DESCRIPTION: PRIMER (v)    FRAGMENT TYPE : Internal (ix)    FEATURE
- (D) OTHER INFORMATION:  
  I is inosine  
  K is G or T/U  
  R is G or A (xi)    SEQUENCE DESCRIPTION: SEQ ID NO:8:

TCATIGCKKC RAKIGGTTC          19

(2) INFORMATION FOR SEQ ID NO:9:

(i)    SEQUENCE CHARACTERISTICS:
- (A) LENGTH: 20 base pairs
- (B) TYPE: nucleic acid
- (C) STRANDEDNESS: single
- (D) TOPOLOGY: linear

UNITED STATES PATENT AND TRADEMARK OFFICE
CERTIFICATE OF CORRECTION

PATENT NO.   : 5,874,269
DATED        : February 23, 1999
INVENTOR(S)  : John I. Stiles, Istefo Moisyadi & Kabi Raj Neupane It is certified that error appears in the above-identified patent and that said Letters Patent is hereby corrected as shown below:

(ii)    MOLECULE TYPE: OTHER NUCLEIC ACID
           (A)    DESCRIPTION: PRIMER (v)    FRAGMENT TYPE : Internal (xi)    SEQUENCE DESCRIPTION: SEQ ID NO:9:

GACACTGTGG AGAGGCTGAC           20 --.

Signed and Sealed this

Twenty-seventh Day of November, 2001

Attest:

NICHOLAS P. GODICI
*Attesting Officer*    *Acting Director of the United States Patent and Trademark Office*